US011071500B2

(12) United States Patent
Cheng et al.

(10) Patent No.: US 11,071,500 B2
(45) Date of Patent: Jul. 27, 2021

(54) IDENTIFICATION OF FALSE ASYSTOLE DETECTION

(71) Applicant: Medtronic, Inc., Minneapolis, MN (US)

(72) Inventors: Ya-Jian Cheng, Lino Lakes, MN (US); Jerry D. Reiland, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 131 days.

(21) Appl. No.: 16/401,553

(22) Filed: May 2, 2019

(65) Prior Publication Data

US 2020/0345309 A1 Nov. 5, 2020

(51) Int. Cl.
*A61B 5/287* (2021.01)
*A61B 5/00* (2006.01)
*A61B 5/364* (2021.01)

(52) U.S. Cl.
CPC ............ *A61B 5/7221* (2013.01); *A61B 5/287* (2021.01); *A61B 5/364* (2021.01)

(58) Field of Classification Search
CPC ... A61B 5/04012; A61B 5/042; A61B 5/0422; A61B 5/0456; A61B 5/0464; A61B 5/0468; A61B 5/686; A61B 5/7207; A61B 5/7221; A61B 5/746; A61B 5/283; A61B 5/287; A61B 5/316; A61B 5/352; A61B 5/363; A61B 5/364
See application file for complete search history.

(56) References Cited

U.S. PATENT DOCUMENTS

| 4,428,378 | A  | 1/1984  | Anderson et al. |
| 5,052,388 | A  | 10/1991 | Sivula et al. |
| 5,117,824 | A  | 6/1992  | Keimel et al. |
| 6,980,675 | B2 | 12/2005 | Evron et al. |
| 7,286,866 | B2 | 10/2007 | Okerlund et al. |
| 7,308,297 | B2 | 12/2007 | Reddy et al. |
| 7,308,299 | B2 | 12/2007 | Burrell et al. |
| 7,321,677 | B2 | 1/2008  | Evron et al. |
| 7,346,381 | B2 | 3/2008  | Okerlund et al. |
| 7,454,248 | B2 | 11/2008 | Burrell et al. |
| 7,499,743 | B2 | 3/2009  | Vass et al. |
| 7,565,190 | B2 | 7/2009  | Okerlund et al. |

(Continued)

FOREIGN PATENT DOCUMENTS

WO  2013054242 A1  4/2013

OTHER PUBLICATIONS

International Search Report and Written Opinion of International Application No. PCT/US2020/024581, dated Jul. 14, 2020, 8 pp.

(Continued)

*Primary Examiner* — George Manuel
(74) *Attorney, Agent, or Firm* — Shumaker & Sieffert, P.A.

(57) ABSTRACT

This disclosure is directed to techniques for identifying false detection of asystole in a cardiac electrogram that include determining whether at least one of a plurality of false asystole detection criteria are satisfied. In some examples, the plurality of false asystole detection criteria includes a first false asystole detection criterion including a reduced amplitude threshold for detecting cardiac depolarizations in the cardiac electrogram, and a second false asystole detection criterion for detecting decaying noise in the cardiac electrogram.

23 Claims, 20 Drawing Sheets

(56) References Cited

U.S. PATENT DOCUMENTS

| | | | |
|---|---|---|---|
| 7,587,074 | B2 | 9/2009 | Zarkh et al. |
| 7,599,730 | B2 | 10/2009 | Hunter et al. |
| 7,613,500 | B2 | 11/2009 | Vass et al. |
| 7,684,863 | B2 | 3/2010 | Parikh et al. |
| 7,742,629 | B2 | 6/2010 | Zarkh et al. |
| 7,747,047 | B2 | 6/2010 | Okerlund et al. |
| 7,778,685 | B2 | 8/2010 | Evron et al. |
| 7,778,686 | B2 | 8/2010 | Vass et al. |
| 7,813,785 | B2 | 10/2010 | Okerlund et al. |
| 7,996,063 | B2 | 8/2011 | Vass et al. |
| 8,060,185 | B2 | 11/2011 | Hunter et al. |
| 8,180,428 | B2 | 5/2012 | Kaiser et al. |
| 8,401,616 | B2 | 3/2013 | Verard et al. |
| 8,977,350 | B2 | 3/2015 | Sarkar et al. |
| 9,320,446 | B2 | 4/2016 | Gillberg et al. |
| 9,474,457 | B2 | 10/2016 | Ghosh et al. |
| 9,486,151 | B2 | 11/2016 | Ghosh et al. |
| 9,901,276 | B2 | 2/2018 | Sarkar |
| 9,936,890 | B2 | 4/2018 | Sarkar et al. |
| 2004/0049120 | A1 | 3/2004 | Cao et al. |
| 2005/0008210 | A1 | 1/2005 | Evron et al. |
| 2006/0074285 | A1 | 4/2006 | Zarkh et al. |
| 2008/0269813 | A1* | 10/2008 | Greenhut ............ A61B 5/042 607/5 |
| 2009/0099619 | A1 | 4/2009 | Lessmeier et al. |
| 2011/0066203 | A1 | 3/2011 | Rosenberg et al. |
| 2011/0112398 | A1 | 5/2011 | Zarkh et al. |
| 2011/0184297 | A1 | 7/2011 | Vitali et al. |
| 2011/0196247 | A1 | 8/2011 | Cao et al. |
| 2011/0319777 | A1 | 12/2011 | Mehrotra et al. |
| 2012/0029373 | A1 | 2/2012 | Stadler et al. |
| 2012/0283587 | A1 | 11/2012 | Gosh et al. |
| 2012/0284003 | A1 | 11/2012 | Gosh et al. |
| 2013/0116739 | A1 | 5/2013 | Brada et al. |
| 2014/0276928 | A1 | 9/2014 | Vanderpool et al. |
| 2014/0323882 | A1 | 10/2014 | Ghosh et al. |
| 2014/0323892 | A1 | 10/2014 | Ghosh et al. |
| 2014/0371832 | A1 | 12/2014 | Ghosh et al. |
| 2014/0371833 | A1 | 12/2014 | Ghosh et al. |
| 2015/0157231 | A1 | 6/2015 | Gillberg et al. |
| 2015/0157232 | A1 | 6/2015 | Gillberg et al. |
| 2015/0157865 | A1 | 6/2015 | Gillberg et al. |
| 2016/0030751 | A1 | 2/2016 | Ghosh et al. |
| 2016/0045737 | A1 | 2/2016 | Ghosh et al. |
| 2016/0045738 | A1 | 2/2016 | Ghosh et al. |
| 2016/0045744 | A1 | 2/2016 | Gillberg et al. |
| 2017/0273589 | A1 | 9/2017 | Sarkar et al. |
| 2018/0028083 | A1 | 2/2018 | Greenhut et al. |
| 2018/0028086 | A1 | 2/2018 | Cao et al. |
| 2018/0264258 | A1 | 9/2018 | Cheng et al. |

OTHER PUBLICATIONS

Sweeney, et al., "Analysis of Ventricular Activation Using Surface Electrocardiography to Predict Left Ventricular Reverse Volumetric Remolding During Cardiac Resynchronization Theraphy," Circulation, Journal of the American Heart Association, 2010:121:626-634, originally published online Jan. 25, 2010, (10 pages).

Van Deursen et al., "Vectrocardiography as a Tool for Easy Optimization of Cardiac Resynchronization Therapy in Canine Left Bundle Branch Block Hearts," Circulation Arrhythmia and Electrophysiology, 2012:5:544-552, originally published online Apr. 24, 2012, (10 pages).

Ryu, et al., "Simultaneous Electrical and Mechanical Mapping Using 3d Cardiac Mapping System: Novel Approach for Optimal Cardiac Resynchronization Therapy," Journal of Cardiovascular Electrophysiology, Feb. 2010, vol. 21, Vo. 2, pp. 219-222. (4 pages).

Sperzel, et al., "Intraoperative Characterization of Interventricular Mechanical Dyssynchrony Using Electroanatomic Mapping System—A Feasibility Study," Journal of Interventional Cardiac Electrophysiology, published online Jun. 14, 2012, 35(2); (8 pages).

* cited by examiner

IDENTIFICATION OF FALSE ASYSTOLE DETECTION

FIELD

The disclosure relates generally to medical systems and, more particularly, medical systems configured to detect asystole based on a cardiac electrogram.

BACKGROUND

Some types of medical devices may monitor a cardiac electrogram (EGM) of a patient to monitor the electrical activity of the patient's heart. A cardiac EGM is an electrical signal sensed via electrodes. In some examples, the medical devices monitor a cardiac EGM to detect one or more types of arrhythmia, such as bradycardia, tachycardia, fibrillation, or asystole (e.g., caused by sinus pause or AV block).

SUMMARY

A cardiac EGM may include noise in addition to the signal representing the electrical activity of the heart. Additionally, the amplitude of the signal representing the electrical activity of the heart within the cardiac EGM may vary over time, e.g., due to movement of the electrodes relative to the cardiac tissue. Noise and signal amplitude variations may confound detection of arrhythmias, such as asystole, using the cardiac EGM.

In general, the disclosure is directed to techniques for identifying false detection of asystole in a cardiac electrogram. The techniques include analyzing the cardiac EGM to determine whether at least one of a plurality of false asystole detection criteria are satisfied. In some examples, processing circuitry of a medical device system performs this analysis in response to an asystole detection criterion being satisfied, and may determine whether to provide or withhold an indication (e.g., to a clinician or other user) that the patient experienced asystole based on the analysis. In this manner, the techniques of this disclosure may advantageously enable improved accuracy in the identification of true asystole and, consequently, better evaluation of the condition of the patient.

In one example, a medical system comprises a plurality of electrodes configured to sense a cardiac electrogram of a patient; and processing circuitry. The processing circuitry is configured to determine that an asystole detection criterion is satisfied based on the cardiac electrogram and, based on the determination that the asystole detection is satisfied, determine whether a plurality of false asystole detection criteria are satisfied based on the cardiac electrogram signal. The processing circuitry is further configured to withhold an indication of an asystole episode for the patient based on a determination that at least one of the plurality of false asystole detection criteria is satisfied. The plurality of false asystole detection criteria comprises a first false asystole detection criterion including a reduced amplitude threshold for detecting cardiac depolarizations in the cardiac electrogram, and a second false asystole detection criterion for detecting decaying noise in the cardiac electrogram.

In another example, a method comprises sensing a cardiac electrogram of a patient via a plurality of electrodes of a medical system, and determining, by processing circuitry of the medical system, that an asystole detection criterion is satisfied based on the cardiac electrogram. The method further comprises, based on the determination that the asystole detection is satisfied, determining, by the processing circuitry, that at least one of a plurality of false asystole detection criteria are satisfied based on the cardiac electrogram signal, and withholding, by the processing circuitry, an indication of an asystole episode for the patient based on a determination that at least one of the plurality of false asystole detection criteria is satisfied. The plurality of false asystole detection criteria comprises a first false asystole detection criterion including a reduced amplitude threshold for detecting cardiac depolarizations in the cardiac electrogram, and a second false asystole detection criterion for detecting decaying noise in the cardiac electrogram.

In another example, a non-transitory computer-readable storage medium comprises program instructions that, when executed by processing circuitry of a medical system, cause the processing circuitry to determine that an asystole detection criterion is satisfied based on a cardiac electrogram sensed via a plurality of electrodes of the medical system. Based on the determination that the asystole detection is satisfied, the program instructions cause the processing circuitry to determine whether a plurality of false asystole detection criteria are satisfied based on the cardiac electrogram signal, and withhold an indication of an asystole episode for the patient based on a determination that at least one of the plurality of false asystole detection criteria is satisfied. The plurality of false asystole detection criteria comprises a first false asystole detection criterion including a reduced amplitude threshold for detecting cardiac depolarizations in the cardiac electrogram, and a second false asystole detection criterion for detecting decaying noise in the cardiac electrogram.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF THE DRAWINGS

Like reference characters denote like elements throughout the description and figures.

DETAILED DESCRIPTION

Figure 1:
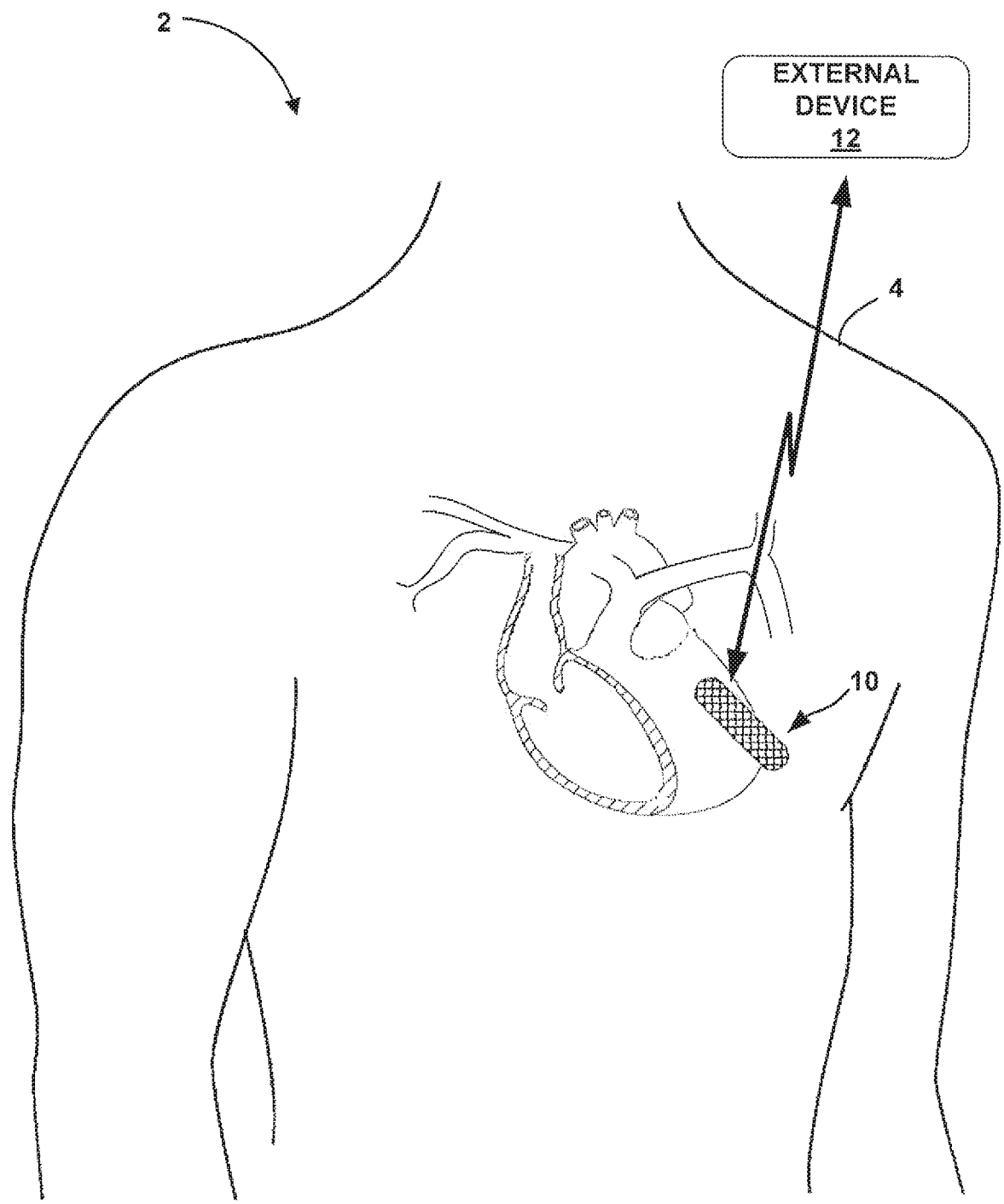
FIG. 1 illustrates the environment of an example medical system in conjunction with a patient.

A variety of types of medical devices sense cardiac EGMs. Some medical devices that sense cardiac EGMs are non-invasive, e.g., using a plurality of electrodes placed in contact with external portions of the patient, such as at various locations on the skin of the patient. The electrodes used to monitor the cardiac EGM in these non-invasive processes may be attached to the patient using an adhesive, strap, belt, or vest, as examples, and electrically coupled to a monitoring device, such as an electrocardiograph, Holter monitor, or other electronic device. The electrodes are configured to sense electrical signals associated with the electrical activity of the heart or other cardiac tissue of the patient, and to provide these sensed electrical signals to the electronic device for further processing and/or display of the electrical signals. The non-invasive devices and methods may be utilized on a temporary basis, for example to monitor a patient during a clinical visit, such as during a doctor's appointment, or for example for a predetermined period of time, for example for one day (twenty-four hours), or for a period of several days.

External devices that may be used to non-invasively sense and monitor cardiac EGMs include wearable devices with electrodes configured to contact the skin of the patient, such as patches, watches, or necklaces. One example of a wearable physiological monitor configured to sense a cardiac EGM is the SEEQ™ Mobile Cardiac Telemetry System, available from Medtronic plc, of Dublin, Ireland. Such external devices may facilitate relatively longer-term monitoring of patients during normal daily activities, and may periodically transmit collected data to a network service, such as the Medtronic Carelink™ Network.

Implantable medical devices (IMDs) also sense and monitor cardiac EGMs. The electrodes used by IMDs to sense cardiac EGMs are typically integrated with a housing of the IMD and/or coupled to the IMD via one or more elongated leads. Example IMDs that monitor cardiac EGMs include pacemakers and implantable cardioverter-defibrillators, which may be coupled to intravascular or extravascular leads, as well as pacemakers with housings configured for implantation within the heart, which may be leadless. An example of pacemaker configured for intracardiac implantation is the Micra™ Transcatheter Pacing System, available from Medtronic plc. Some IMDs that do not provide therapy, e.g., implantable patient monitors, sense cardiac EGMs. One example of such an IMD is the Reveal LINQ™ Insertable Cardiac Monitor, available from Medtronic plc, which may be inserted subcutaneously. Such IMDs may facilitate relatively longer-term monitoring of patients during normal daily activities, and may periodically transmit collected data to a network service, such as the Medtronic Carelink™ Network.

Regardless of which type or types of devices are used, a noise signal, which may be referred to as an artifact, may appear in the cardiac EGM. The time duration of the noise signal may extend over a portion of a normal timeframe for a cardiac cycle of the heart, or may extend over a time span during which multiple cardiac cycles may be expected to have occurred. Such noise signals may be more prevalent when cutaneous, subcutaneous, or extravascular electrodes are used to sense the cardiac EGM, e.g., due to temporary change in contact between at least one of the electrodes and the tissue where the electrode is located due to relative motion of the electrode and tissue. In some examples, the noise signal manifests as a baseline drift of the cardiac EGM, and may include a portion that decays back towards the steady-state baseline.

The presence of a noise signal in a sensed cardiac EGM may cause circuitry for detecting depolarizations, e.g., R-waves, to wrongly detect the noise signal as a depolarization. The noise signal may also cause the circuitry to then fail to sense a number of subsequent depolarizations because the noise signal may be much bigger in amplitude than the subsequent depolarizations and, in some cases, because the high-amplitude noise may cause an adjustable sensing threshold used by the circuitry to be adjusted to a level greater than the amplitude of the true depolarizations. Additionally, the amplitude of the cardiac signals, e.g., depolarizations, within the sensed cardiac EGM may vary over time, e.g., due to respiration. Such cardiac signal amplitude variation may also be more prevalent in cardiac EGMs sensed using cutaneous, subcutaneous, or extravascular electrodes. Variation in cardiac signal amplitude may also cause depolarizations to temporarily fall below a sensing threshold and, consequently, not be detected.

These types of improper sensing of depolarizations may lead to improper analysis of the actual cardiac activity occurring with respect to the patient being monitored. For example, these types of improper sensing of depolarizations may potentially trigger a false-positive indication of a cardiac event, such as asystole, that is not actually occurring in the patient. Such false-positive indications could lead to incorrect assessment of the patient condition, including provision of therapy and/or sending false alerts to medical personnel responsible for the care of the patient being monitored. Low pass filtering of the cardiac EGM will generally not help solve these problems because these types of noise signals and amplitude variations may occur at frequencies near or below that of the cardiac signals.

Medical systems according to this disclosure implement techniques for identifying false detection of asystole in cardiac EGMs by, for example, detecting the presence of noise signals and cardiac signal amplitude variations. In some examples, processing circuitry of the systems analyzes a cardiac EGM associated with an identified asystole episode to determine whether one or more of a plurality of false asystole detection criteria are satisfied. Each of the false asystole detection criteria may be configured to detect one or more indicators of noise and/or amplitude variations in the cardiac EGM.

In some examples, processing circuitry of a medical system performs this analysis in response to an asystole detection criterion being satisfied, and may determine whether to provide or withhold an indication (e.g., to a clinician or other user) that the patient experienced asystole based on the analysis. The processing circuitry may perform the techniques of this disclosure substantially in real-time in response to the detection of asystole, or during a later review of cardiac EGM data for episodes that were identified as asystole. In either case, the processing circuitry may include the processing circuitry of medical device that detected the asystole episode and/or processing circuitry of another device, such as a local or remote computing device which retrieved the episode data from the medical device. In this manner, the techniques of this disclosure may advantageously enable improved accuracy in the identification of true asystole and, consequently, better evaluation of the condition of the patient.

FIG. 1 illustrates the environment of an example medical system 2 in conjunction with a patient 4, in accordance with one or more techniques of this disclosure. The example techniques may be used with an IMD 10, which may be in wireless communication with at least one of external device 12 and other devices not pictured in FIG. 1. In some examples, IMD 10 is implanted outside of a thoracic cavity of patient 4 (e.g., subcutaneously in the pectoral location illustrated in FIG. 1). IMD 10 may be positioned near the sternum near or just below the level of the heart of patient 4, e.g., at least partially within the cardiac silhouette. IMD 10 includes a plurality of electrodes (not shown in FIG. 1), and is configured to sense a cardiac EGM via the plurality of electrodes. In some examples, IMD 10 takes the form of the LINQ™ ICM.

External device 12 may be a computing device with a display viewable by the user and an interface for providing input to external device 12 (i.e., a user input mechanism). In some examples, external device 12 may be a notebook computer, tablet computer, workstation, one or more servers, cellular phone, personal digital assistant, or another computing device that may run an application that enables the computing device to interact with IMD 10.

External device 12 is configured to communicate with IMD 10 and, optionally, another computing device (not illustrated in FIG. 1), via wireless communication. External device 12, for example, may communicate via near-field communication technologies (e.g., inductive coupling, NFC or other communication technologies operable at ranges less than 10-20 cm) and far-field communication technologies (e.g., radiofrequency (RF) telemetry according to the 802.11 or Bluetooth® specification sets, or other communication technologies operable at ranges greater than near-field communication technologies).

External device 12 may be used to configure operational parameters for IMD 10. External device 12 may be used to retrieve data from IMD 10. The retrieved data may include values of physiological parameters measured by IMD 10, indications of episodes of arrhythmia or other maladies detected by IMD 10, and physiological signals recorded by IMD 10. For example, external device 12 may retrieve cardiac EGM segments recorded by IMD 10 due to IMD 10 determining that an episode of asystole or another malady occurred during the segment. As will be discussed in greater detail below with respect to FIG. 5, one or more remote computing devices may interact with IMD 10 in a manner similar to external device 12, e.g., to program IMD 10 and/or retrieve data from IMD 10, via a network.

Processing circuitry of medical system 2, e.g., of IMD 10, external device 12, and/or of one or more other computing devices, may be configured to perform the example techniques for identifying false detection of asystole of this disclosure. In some examples, the processing circuitry of medical system 2 analyzes a cardiac EGM sensed by IMD 10 and associated with an identified asystole episode to determine whether one or more of a plurality of false asystole detection criteria are satisfied. Each of the false asystole detection criteria may be configured to detect one or more indicators of noise and/or amplitude variations in the cardiac EGM. Although described in the context of examples in which IMD 10 that senses the cardiac EGM comprises an insertable cardiac monitor, example systems including one or more implantable or external devices of any type configured to sense a cardiac EGM may be configured to implement the techniques of this disclosure.

Figure 2:
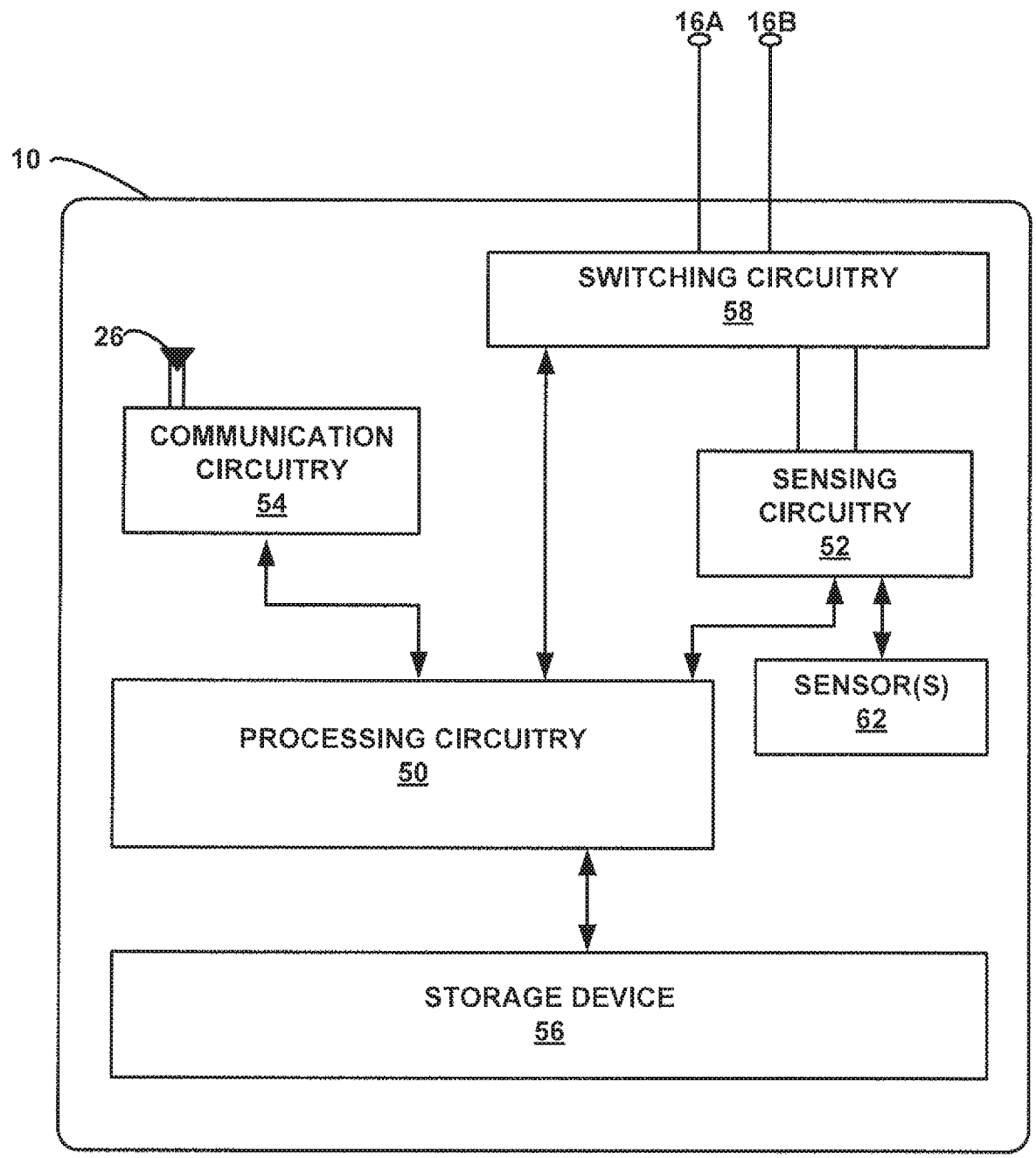
FIG. 2 is a functional block diagram illustrating an example configuration of the implantable medical device (IMD) of the medical system of FIG. 1.

FIG. 2 is a functional block diagram illustrating an example configuration of IMD 10 of FIG. 1 in accordance with one or more techniques described herein. In the illustrated example, IMD 10 includes electrodes 16A and 16B (collectively "electrodes 16"), antenna 26, processing circuitry 50, sensing circuitry 52, communication circuitry 54, storage device 56, switching circuitry 58, and sensors 62. Although the illustrated example includes two electrodes 16, IMDs including or coupled to more than two electrodes 16 may implement the techniques of this disclosure in some examples.

Processing circuitry 50 may include fixed function circuitry and/or programmable processing circuitry. Processing circuitry 50 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 50 may include multiple components, such as any combination of one or more microprocessors, one or more controllers, one or more DSPs, one or more ASICs, or one or more FPGAs, as well as other discrete or integrated logic circuitry. The functions attributed to processing circuitry 50 herein may be embodied as software, firmware, hardware or any combination thereof.

Sensing circuitry 52 may be selectively coupled to electrodes 16 via switching circuitry 58, e.g., to select the electrodes 16 and polarity, referred to as the sensing vector, used to sense a cardiac EGM, as controlled by processing circuitry 50. Sensing circuitry 52 may sense signals from electrodes 16, e.g., to produce a cardiac EGM, in order to facilitate monitoring the electrical activity of the heart. Sensing circuitry 52 also may monitor signals from sensors 62, which may include one or more accelerometers, pressure sensors, and/or optical sensors, as examples. In some examples, sensing circuitry 52 may include one or more filters and amplifiers for filtering and amplifying signals received from electrodes 16 and/or sensors 62.

Sensing circuitry 52 and/or processing circuitry 50 may be configured to detect cardiac depolarizations (e.g., P-waves or R-waves) when the cardiac EGM amplitude crosses a sensing threshold. In some examples, the sensing threshold is automatically adjustable over time using any of a variety of automatic sensing threshold adjustment techniques known in the art. For example, in response to detection of a cardiac depolarization, the sensing threshold for detecting a subsequent cardiac depolarization may decay from an initial value over a period of time. Sensing circuitry 52 and/or processing circuitry 50 may determine the initial value based on the amplitude of detected cardiac depolarization. The initial value and decay of the adjustable sensing threshold may be configured such that the sensing threshold is relatively higher soon after the detected cardiac depolarization when a subsequent depolarization is not expected, and decays to relatively lower values over time as the occurrence of a cardiac depolarization becomes more likely. For cardiac depolarization detection, sensing circuitry 52 may include a rectifier, filter, amplifier, comparator, and/or analog-to-digital converter, in some examples.

In some examples, sensing circuitry 52 may output an indication to processing circuitry 50 in response to sensing of a cardiac depolarization. In this manner, processing circuitry 50 may receive detected cardiac depolarization indicators corresponding to the occurrence of detected R-waves and P-waves in the respective chambers of heart. Processing circuitry 50 may use the indications of detected R-waves and P-waves for determining heart rate and detecting arrhythmias, such as tachyarrhythmias and asystole.

Processing circuitry 50 may detect an asystole episode based on determining that the cardiac electrogram satisfies an asystole detection criterion. The asystole detection criterion may be absence of a cardiac depolarization for a threshold period of time. In such examples, processing circuitry 50 may determine that the cardiac EGM satisfies the asystole detection criterion based on reaching a predetermined time interval from detection of a cardiac depolarization without receiving another cardiac depolarization indication from sensing circuitry 52.

Sensing circuitry 52 may also provide one or more digitized cardiac EGM signals to processing circuitry 50 for analysis, e.g., for use in cardiac rhythm discrimination, and/or for analysis to determine whether one or more false asystole detection criteria are satisfied according to the techniques of this disclosure. In some examples, based on satisfaction of the asystole detection criterion, processing circuitry 50 may store a segment of the digitized cardiac EGM corresponding to the suspected asystole as episode data in storage device 56. The digitized cardiac EGM segment may include samples of the cardiac EGM spanning the period of time for which sensing circuitry 52 did not indicate detection of a depolarization, as well as a period of time before and/or after this period of time during which depolarizations were detected. Processing circuitry 50 of IMD 10, and/or processing circuitry of another device that retrieves the episode data from IMD 10, may analyze the cardiac EGM segment to determine whether one or more false asystole detection criteria are satisfied according to the techniques of this disclosure Communication circuitry 54 may include any suitable hardware, firmware, software or any combination thereof for communicating with another device, such as external device 12, another networked computing device, or another IMD or sensor. Under the control of processing circuitry 50, communication circuitry 54 may receive downlink telemetry from, as well as send uplink telemetry to external device 12 or another device with the aid of an internal or external antenna, e.g., antenna 26. In addition, processing circuitry 50 may communicate with a networked computing device via an external device (e.g., external device 12) and a computer network, such as the Medtronic CareLink® Network. Antenna 26 and communication circuitry 54 may be configured to transmit and/or receive signals via inductive coupling, electromagnetic coupling, Near Field Communication (NFC), Radio Frequency (RF) communication, Bluetooth, WiFi, or other proprietary or non-proprietary wireless communication schemes.

In some examples, storage device 56 includes computer-readable instructions that, when executed by processing circuitry 50, cause IMD 10 and processing circuitry 50 to perform various functions attributed to IMD 10 and processing circuitry 50 herein. Storage device 56 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Storage device 56 may store, as examples, programmed values for one or more operational parameters of IMD 10 and/or data collected by IMD 10 for transmission to another device using communication circuitry 54. Data stored by storage device 56 and transmitted by communication circuitry 54 to one or more other devices may include episode data for suspected asystoles and/or indications that suspected asystoles satisfied one or more false asystole detection criteria.

Figure 3:
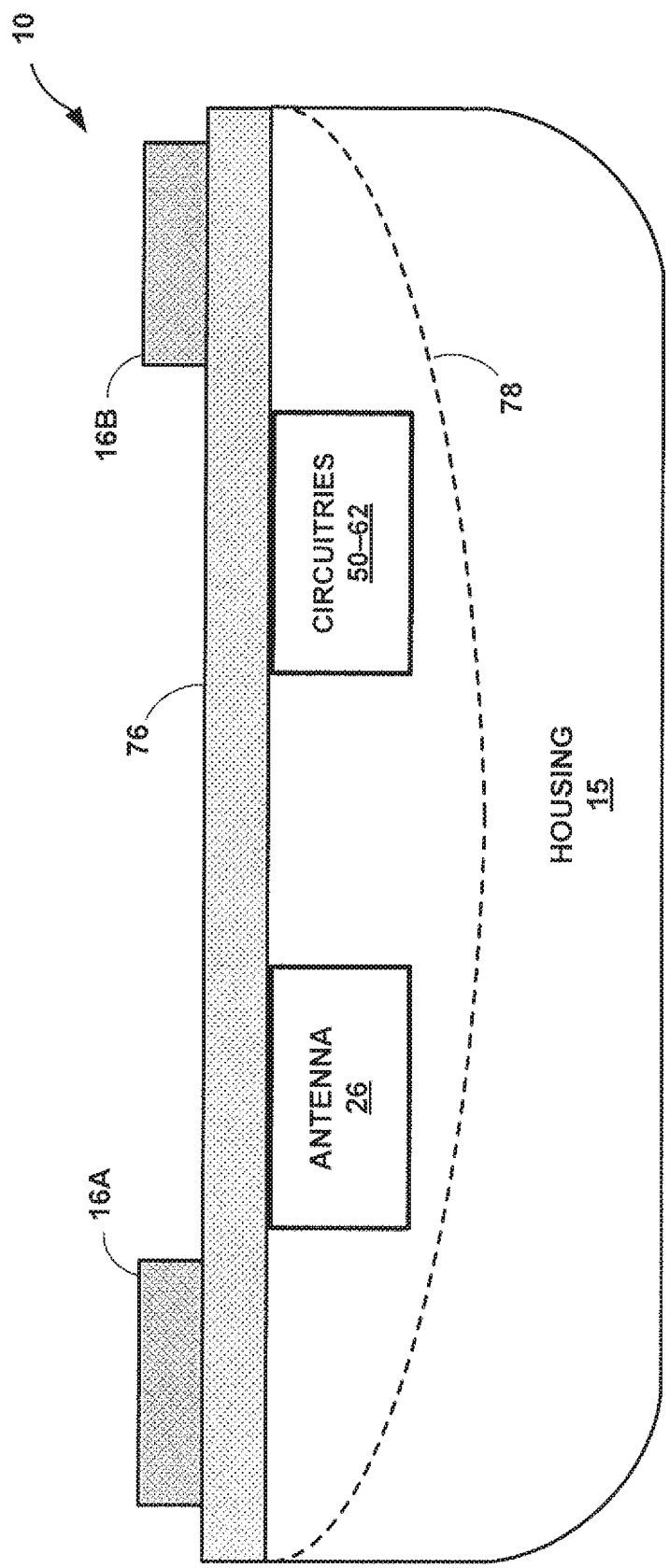
FIG. 3 is a conceptual side-view diagram illustrating an example configuration of the IMD of FIGS. 1 and 2.

FIG. 3 is a conceptual side-view diagram illustrating an example configuration of IMD 10 of FIGS. 1 and 2. In the example shown in FIG. 3, IMD 10 may include a leadless, subcutaneously-implantable monitoring device having a housing 15 and an insulative cover 76. Electrode 16A and electrode 16B may be formed or placed on an outer surface of cover 76. Circuitries 50-62, described above with respect to FIG. 2, may be formed or placed on an inner surface of cover 76, or within housing 15. In the illustrated example, antenna 26 is formed or placed on the inner surface of cover 76, but may be formed or placed on the outer surface in some examples. In some examples, insulative cover 76 may be positioned over an open housing 15 such that housing 15 and cover 76 enclose antenna 26 and circuitries 50-62, and protect the antenna and circuitries from fluids such as body fluids.

One or more of antenna 26 or circuitries 50-62 may be formed on the inner side of insulative cover 76, such as by using flip-chip technology. Insulative cover 76 may be flipped onto a housing 15. When flipped and placed onto housing 15, the components of IMD 10 formed on the inner side of insulative cover 76 may be positioned in a gap 78 defined by housing 15. Electrodes 16 may be electrically connected to switching circuitry 58 through one or more vias (not shown) formed through insulative cover 76. Insulative cover 76 may be formed of sapphire (i.e., corundum), glass, parylene, and/or any other suitable insulating material. Housing 15 may be formed from titanium or any other suitable material (e.g., a biocompatible material). Electrodes 16 may be formed from any of stainless steel, titanium, platinum, iridium, or alloys thereof. In addition, electrodes 16 may be coated with a material such as titanium nitride or fractal titanium nitride, although other suitable materials and coatings for such electrodes may be used.

Figure 4:
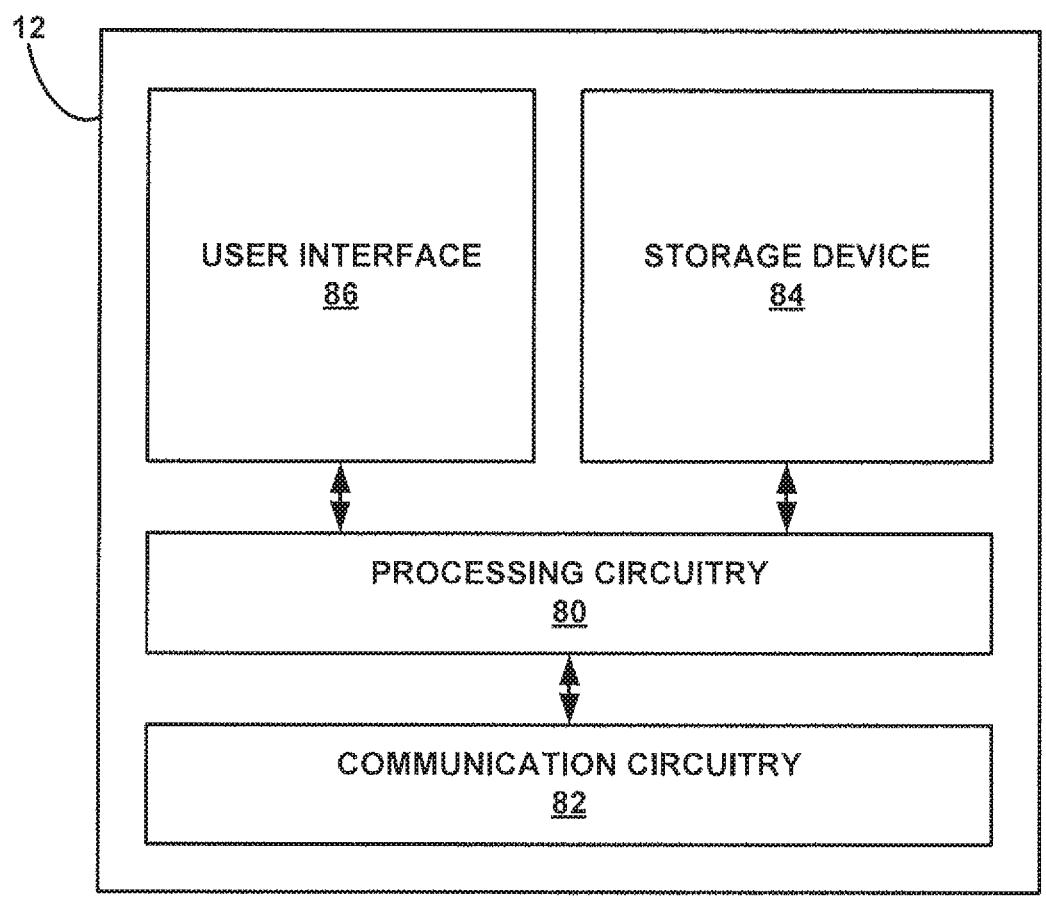
FIG. 4 is a functional block diagram illustrating an example configuration of the external device of FIG. 1.

FIG. 4 is a block diagram illustrating an example configuration of components of external device 12. In the example of FIG. 4, external device 12 includes processing circuitry 80, communication circuitry 82, storage device 84, and user interface 86.

Processing circuitry 80 may include one or more processors that are configured to implement functionality and/or process instructions for execution within external device 12. For example, processing circuitry 80 may be capable of processing instructions stored in storage device 84. Processing circuitry 80 may include, for example, microprocessors, DSPs, ASICs, FPGAs, or equivalent discrete or integrated logic circuitry, or a combination of any of the foregoing devices or circuitry. Accordingly, processing circuitry 80 may include any suitable structure, whether in hardware, software, firmware, or any combination thereof, to perform the functions ascribed herein to processing circuitry 80.

Communication circuitry 82 may include any suitable hardware, firmware, software or any combination thereof for communicating with another device, such as IMD 10. Under the control of processing circuitry 80, communication circuitry 82 may receive downlink telemetry from, as well as send uplink telemetry to, IMD 10, or another device. Communication circuitry 82 may be configured to transmit or receive signals via inductive coupling, electromagnetic coupling, NFC, RF communication, Bluetooth, WiFi, or other proprietary or non-proprietary wireless communication schemes. Communication circuitry 82 may also be configured to communicate with devices other than IMD 10 via any of a variety of forms of wired and/or wireless communication and/or network protocols.

Storage device 84 may be configured to store information within external device 12 during operation. Storage device 84 may include a computer-readable storage medium or computer-readable storage device. In some examples, storage device 84 includes one or more of a short-term memory or a long-term memory. Storage device 84 may include, for example, RAM, DRAM, SRAM, magnetic discs, optical discs, flash memories, or forms of EPROM or EEPROM. In some examples, storage device 84 is used to store data indicative of instructions for execution by processing circuitry 80. Storage device 84 may be used by software or applications running on external device 12 to temporarily store information during program execution.

Data exchanged between external device 12 and IMD 10 may include operational parameters. External device 12 may transmit data including computer readable instructions which, when implemented by IMD 10, may control IMD 10 to change one or more operational parameters and/or export collected data. For example, processing circuitry 80 may transmit an instruction to IMD 10 which requests IMD 10 to export collected data (e.g., asystole episode data) to external device 12. In turn, external device 12 may receive the collected data from IMD 10 and store the collected data in storage device 84. Processing circuitry 80 may implement any of the techniques described herein to analyze cardiac EGMs received from IMD 10, e.g., to determine whether asystole and false asystole criteria are satisfied.

A user, such as a clinician or patient 4, may interact with external device 12 through user interface 86. User interface 86 includes a display (not shown), such as a liquid crystal display (LCD) or a light emitting diode (LED) display or other type of screen, with which processing circuitry 80 may present information related to IMD 10, e.g., cardiac EGMs, indications of detections of arrhythmia episodes, and indications of determinations that one or more false asystole detection criteria were satisfied. In addition, user interface 86 may include an input mechanism configured to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processing circuitry 80 of external device 12 and provide input. In other examples, user interface 86 also includes audio circuitry for providing audible notifications, instructions or other sounds to the user, receiving voice commands from the user, or both.

Figure 5:
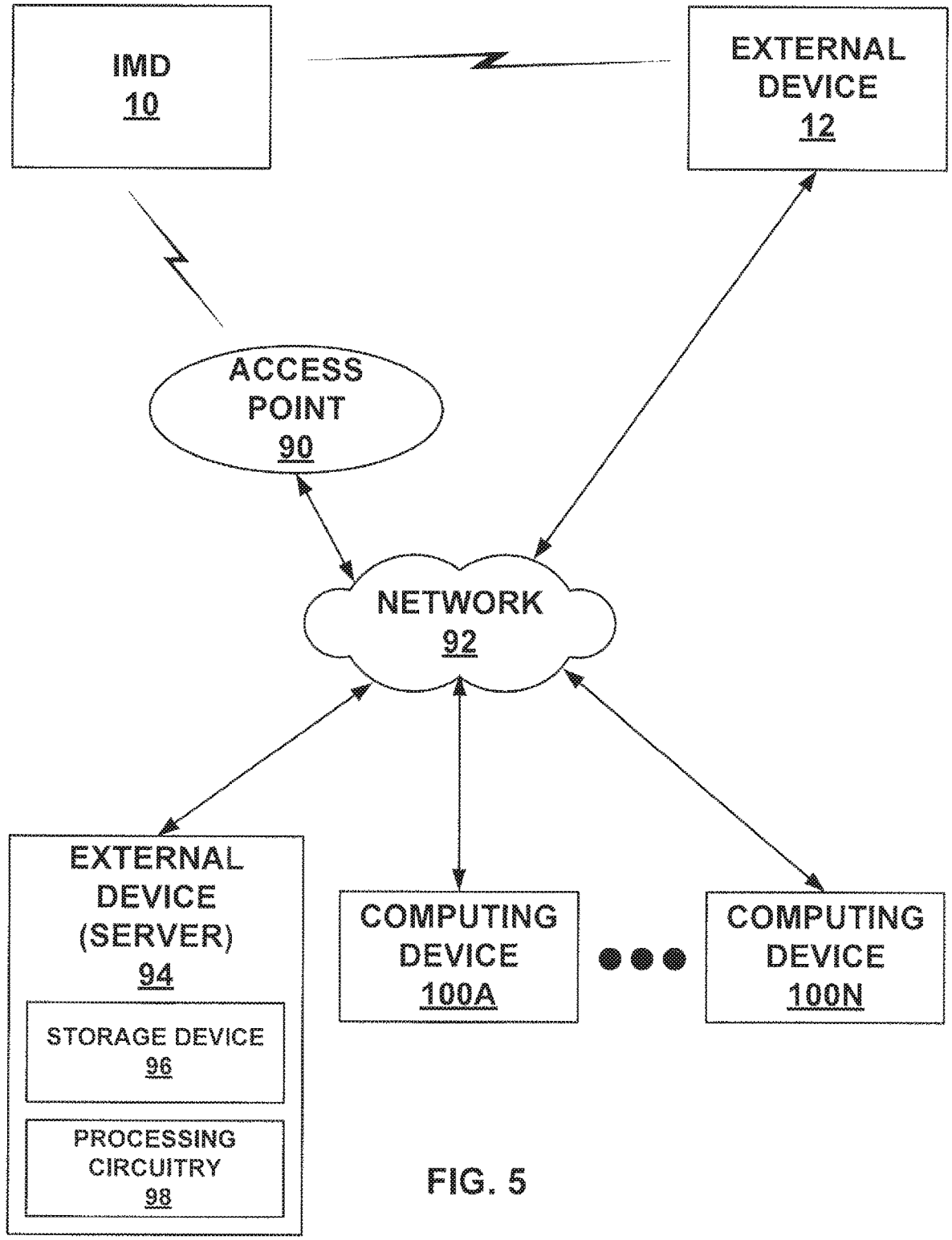
FIG. 5 is a block diagram illustrating an example system that includes an access point, a network, external computing devices, such as a server, and one or more other computing devices, which may be coupled to the IMD and external device of FIGS. 1-4.

FIG. 5 is a block diagram illustrating an example system that includes an access point 90, a network 92, external computing devices, such as a server 94, and one or more other computing devices 100A-100N (collectively, "computing devices 100"), which may be coupled to IMD 10 and external device 12 via network 92, in accordance with one or more techniques described herein. In this example, IMD 10 may use communication circuitry 54 to communicate with external device 12 via a first wireless connection, and to communicate with an access point 90 via a second wireless connection. In the example of FIG. 5, access point 90, external device 12, server 94, and computing devices 100 are interconnected and may communicate with each other through network 92.

Access point 90 may include a device that connects to network 92 via any of a variety of connections, such as telephone dial-up, digital subscriber line (DSL), or cable modem connections. In other examples, access point 90 may be coupled to network 92 through different forms of connections, including wired or wireless connections. In some examples, access point 90 may be a user device, such as a tablet or smartphone, that may be co-located with the patient. IMD 10 may be configured to transmit data, such as asystole episode data and indications that one or more false asystole detection criteria are satisfied, to access point 90. Access point 90 may then communicate the retrieved data to server 94 via network 92.

In some cases, server 94 may be configured to provide a secure storage site for data that has been collected from IMD 10 and/or external device 12. In some cases, server 94 may assemble data in web pages or other documents for viewing by trained professionals, such as clinicians, via computing devices 100. One or more aspects of the illustrated system of FIG. 5 may be implemented with general network technology and functionality, which may be similar to that provided by the Medtronic CareLink® Network.

In some examples, one or more of computing devices 100 may be a tablet or other smart device located with a clinician, by which the clinician may program, receive alerts from, and/or interrogate IMD 10. For example, the clinician may access data collected by IMD 10 through a computing device 100, such as when patient 4 is in in between clinician visits, to check on a status of a medical condition. In some examples, the clinician may enter instructions for a medical intervention for patient 4 into an application executed by computing device 100, such as based on a status of a patient condition determined by IMD 10, external device 12, server 94, or any combination thereof, or based on other patient data known to the clinician. Device 100 then may transmit the instructions for medical intervention to another of computing devices 100 located with patient 4 or a caregiver of patient 4. For example, such instructions for medical intervention may include an instruction to change a drug dosage, timing, or selection, to schedule a visit with the clinician, or to seek medical attention. In further examples, a computing device 100 may generate an alert to patient 4 based on a status of a medical condition of patient 4, which may enable patient 4 proactively to seek medical attention prior to receiving instructions for a medical intervention. In this manner, patient 4 may be empowered to take action, as needed, to address his or her medical status, which may help improve clinical outcomes for patient 4.

In the example illustrated by FIG. 5, server 94 includes a storage device 96, e.g., to store data retrieved from IMD 10, and processing circuitry 98. Although not illustrated in FIG. 5 computing devices 100 may similarly include a storage device and processing circuitry. Processing circuitry 98 may include one or more processors that are configured to implement functionality and/or process instructions for execution within server 94. For example, processing circuitry 98 may be capable of processing instructions stored in storage device 96. Processing circuitry 98 may include, for example, microprocessors, DSPs, ASICs, FPGAs, or equivalent discrete or integrated logic circuitry, or a combination of any of the foregoing devices or circuitry. Accordingly, processing circuitry 98 may include any suitable structure, whether in hardware, software, firmware, or any combination thereof, to perform the functions ascribed herein to processing circuitry 98. Processing circuitry 98 of server 94 and/or the processing circuitry of computing devices 100 may implement any of the techniques described herein to analyze cardiac EGMs received from IMD 10, e.g., to determine whether asystole and false asystole criteria are satisfied.

Storage device 96 may include a computer-readable storage medium or computer-readable storage device. In some examples, storage device 96 includes one or more of a short-term memory or a long-term memory. Storage device 96 may include, for example, RAM, DRAM, SRAM, magnetic discs, optical discs, flash memories, or forms of EPROM or EEPROM. In some examples, storage device 96 is used to store data indicative of instructions for execution by processing circuitry 98.

Figure 6:
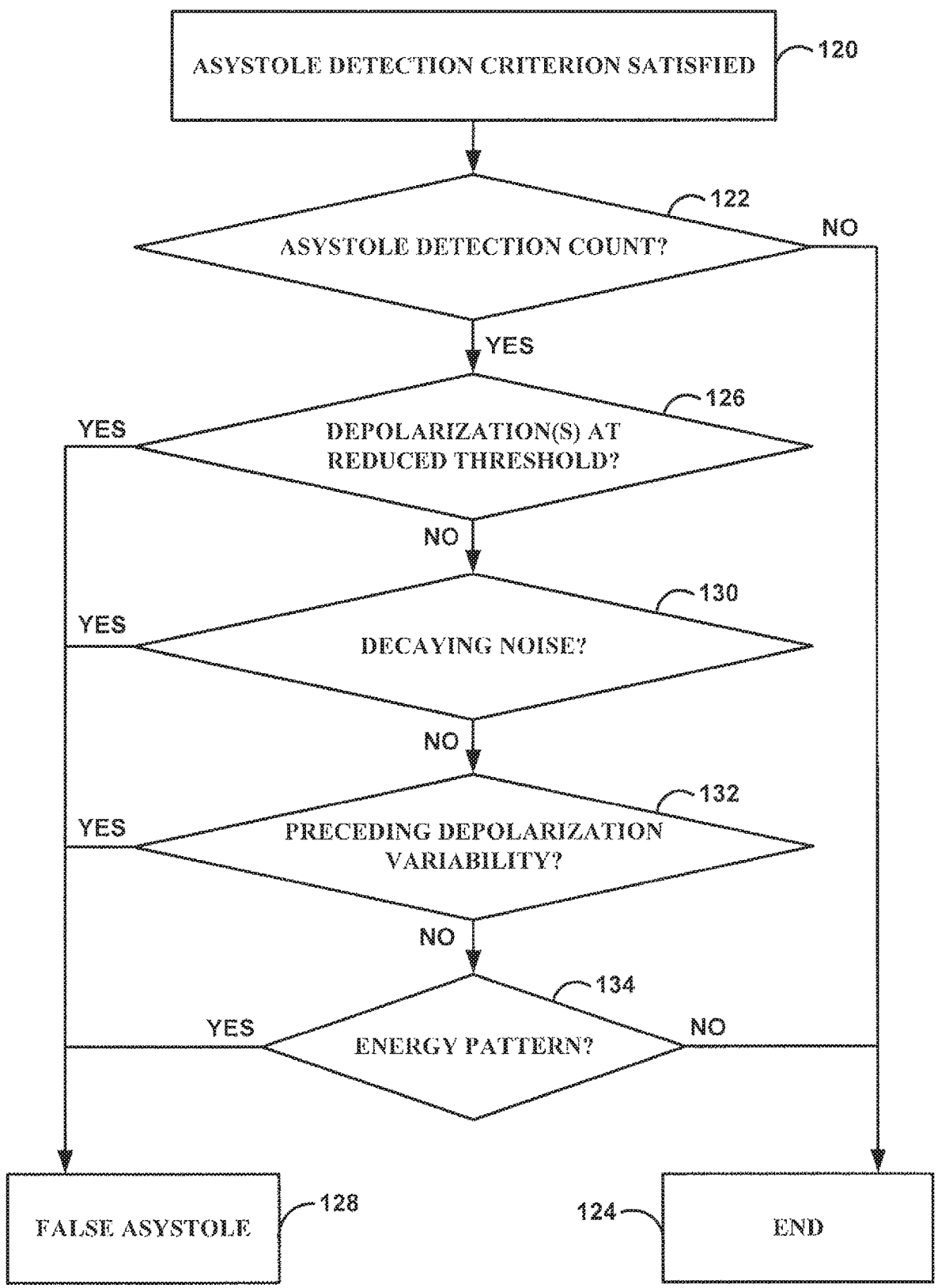
FIG. 6 is a flow diagram illustrating an example operation for determining whether an identification of an asystole episode was false based on whether a plurality of false asystole detection criteria is satisfied.

FIG. 6 is a flow diagram illustrating an example operation for determining whether an identification of an asystole episode was false based on whether a plurality of false asystole detection criteria is satisfied. According to the illustrated example of FIG. 6, processing circuitry 50 of IMD 10 determines that at least one asystole detection criterion is satisfied based on a cardiac EGM sensed by sensing circuitry 52 of IMD 10 (120). For example, as discussed in greater detail with respect to FIG. 2, processing circuitry 50 may determine that a threshold time interval, e.g., 2-3 seconds, has passed since sensing circuitry 52 identified a cardiac depolarization, e.g., R-wave, within the cardiac EGM.

Based on determining that the asystole detection criterion is satisfied, processing circuitry 50 determines whether the one or more of a plurality of false asystole detection criteria are satisfied. In the illustrated example, processing circuitry 50 determines whether a false asystole detection criterion comprising an asystole detection count criterion is satisfied (122). For example, processing circuitry 50 may determine whether the asystole detection criterion was satisfied at least a threshold number of times within a predetermined time period extending back from the most recent satisfaction of the asystole detection criterion, e.g., at least two times within the past thirty days. As another example, processing circuitry may determine whether the asystole detection criterion was satisfied at a threshold rate, e.g., a rate of one asystole per thirty days, over a time period. The time period may be the entire time IMD 10 has been active since implant, or since a period start time other than implant, e.g., a period starting a fixed number of days, weeks, or months after implant, or upon a power on reset or other reset of IMD 10.

Based on determining that the asystole detection count criterion is not satisfied (NO of 122), the example operation of FIG. 6 ends (124). Based on determining that the asystole detection count criterion is satisfied (YES of 122), processing circuitry 50 proceeds to determine whether one or more of the other false asystole detection criteria are satisfied. Implementation of such an asystole detection count criterion is based on an observation that false detection of asystole tends to occur in devices that frequently detect asystole, and to not occur in devices that infrequently detect asystole. Requiring satisfaction for the asystole detection count criterion prior to applying the other false asystole detection criteria, as in the example operation of FIG. 6, may avoid erroneous classification of a suspect asystole as false by the false asystole detection criteria.

Noise signals may occur in the cardiac EGM intermittently or with varying frequency based on, for example, changes in the condition of IMD 10 or patient 4. Consequently, there may be a greater likelihood that a given asystole detection is false (e.g., caused by noise) during a period in which asystole detection is more frequent (indicating that there may be noise in the EGM) than a period in which asystole detection is less frequent. Implementing an asystole detection count criterion to selectively activate and deactivate evaluation of the cardiac EGM of suspected asystole episodes using the false asystole detection criteria described herein may achieve varying emphasis on sensitivity versus specificity for asystole detection depending on the recent frequency of asystole and, thus, the likelihood that most recent asystole episode is false.

During periods in which asystole frequency is below a threshold such that the asystole count criterion is not satisfied, processing circuitry 50 may not activate evaluation of the cardiac EGMs of suspected asystole episodes using the false asystole detection criteria, thereby preserving sensitivity of the asystole detection. During periods in which asystole frequency is above a threshold such that the asystole count criterion is not satisfied, processing circuitry 50 may activate evaluation of the cardiac EGMs of suspected asystole episodes using the false asystole detection criteria, thereby improving specificity of the asystole detection. Selectively (e.g., intermittently) activating and deactivating evaluation of the cardiac EGMs of suspected asystole episodes using the false asystole detection criteria may thus provide a desired balance between sensitivity and specificity for the current condition of the cardiac EGM, e.g., degree of noise in the cardiac EGM.

In the illustrated example, based on determining that the asystole detection count criterion is satisfied (YES of 122), processing circuitry 50 proceeds to determine whether, using a reduced amplitude threshold, a threshold number of depolarizations are detected within the time interval of the cardiac EGM for which depolarizations were not detected using the asystole detection criteria amplitude threshold (126). Based on the depolarizations at reduced amplitude threshold criterion being satisfied (YES of 126), processing circuitry 50 may determine that the suspected asystole episode is a false asystole (128). Based on the depolarizations at reduced amplitude threshold criterion not being satisfied (NO of 126), processing circuitry 50 may proceed to consider another false asystole detection criterion.

In the illustrated example, based on determining that the depolarizations at reduced amplitude threshold criterion is not satisfied (NO of 126), processing circuitry 50 proceeds to determine whether the cardiac EGM associated with the asystole detection criterion being satisfied also satisfies a decaying noise criterion (130). Based on the decaying noise criterion being satisfied (YES of 130), processing circuitry 50 may determine that the suspected asystole episode is a false asystole (128). Based on the decaying noise criterion not being satisfied (NO of 130), processing circuitry 50 may proceed to consider another false asystole detection criterion.

In the illustrated example, based on determining that the decaying noise criterion is not satisfied (NO of 130), processing circuitry 50 proceeds to determine whether the cardiac EGM associated with the suspected asystole episode satisfies a preceding depolarization variability criterion (132). Based on the preceding depolarization variability criterion being satisfied (YES of 132), processing circuitry 50 may determine that the suspected asystole episode is a false asystole (128). Based on the preceding depolarization variability criterion not being satisfied (NO of 132), processing circuitry 50 may proceed to consider another false asystole detection criterion.

In the illustrated example, based on determining that the preceding depolarization variability criterion is not satisfied (NO of 132), processing circuitry 50 proceeds to determine whether the cardiac EGM associated with the suspected asystole episode satisfies an energy pattern criterion (134). Based on the energy pattern criterion being satisfied (YES of 134), processing circuitry 50 may determine that the suspected asystole episode is a false asystole (128). Based on the energy criterion not being satisfied (NO of 134), the example operation of FIG. 6 ends (124).

Based on the example operation of FIG. 6 ending (124), e.g., due to none of the false asystole detection criteria being satisfied, or an insufficient number or combination of the false asystole detection criteria being satisfied, processing circuitry 50 may classify the suspected asystole episode as a true asystole episode. Based on the asystole episode being classified as true, processing circuitry 50 may use the asystole episode in further operations, such as calculating statistics, determining a condition of patient, or transmitting true episode data to other devices. Based on determining that the suspected asystole episode is a false asystole (128), processing circuitry 50 may use the false asystole episode in further operations, such as calculating statistics of false episodes and transmitting false episode data to other devices, e.g., for consideration by a user of a modification of the operation of IMD 10 to avoid further false asystole detection.

The order and flow of the operation illustrated in FIG. 6 is one example. In other examples according to this disclosure, more or fewer false asystole detection criteria may be considered, the false asystole detection criteria may be considered in a different order, or satisfaction of different numbers or combinations of false asystole detection criteria may be required for a determination that the suspected asystole episode was false. Further, in some examples, processing circuitry may perform or not perform the method of FIG. 6, or any of the techniques described herein, as directed by a user, e.g., via external device 12 or computing devices 100. For example, a patient, clinician, or other user may turn on or off functionality for identifying false asystole detection remotely (e.g., using Wi-Fi or cellular services) or locally (e.g., using an application provided on a patient's cellular phone or using a medical device programmer).

Additionally, although described in the context of an example in which IMD 10, and processing circuitry 50 of IMD 10, perform each of the portions of the example operation, the example operation of FIG. 6, as well as the example operations described herein with respect to FIGS. 7-17, may be performed by any processing circuitry of any one or more devices of a medical system, e.g., any combination of one or more of processing circuitry 50 of IMD 10, processing circuitry 80 of external device 12, processing circuitry 98 of server 94, or processing circuitry of computing devices 100. In some examples, processing circuitry 50 of IMD 10 may determine whether an asystole detection criterion is satisfied, and provide episode data for the suspected asystole episodes to another device. In such examples, processing circuitry of the other device, e.g., external device 12, server 94, or a computing device 100, may apply one or more false asystole detection criteria to the episode data.

Figure 7:
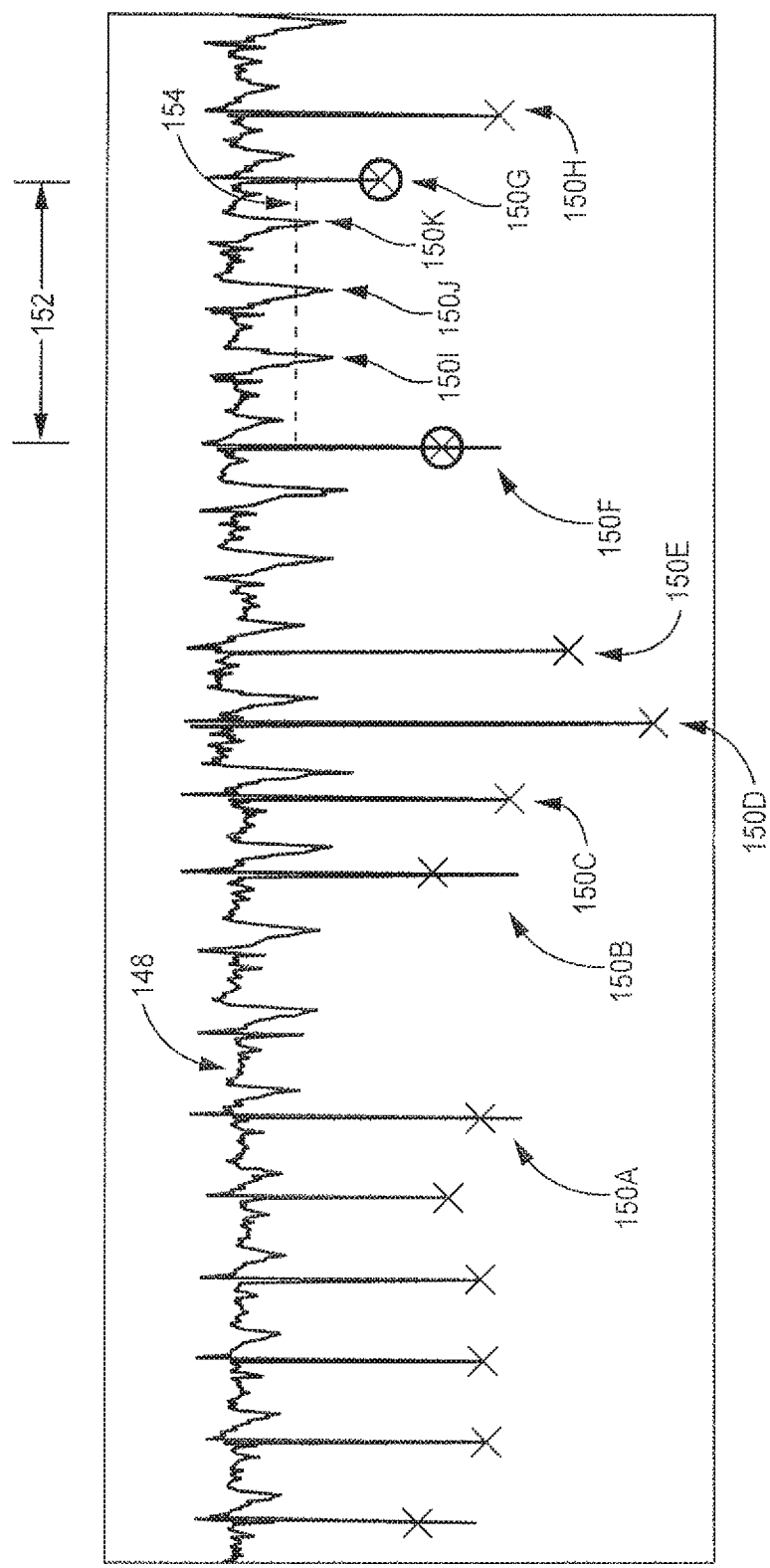
FIG. 7 is a graph illustrating a cardiac EGM associated with an identified asystole episode and an example technique for determining whether an example false asystole detection criterion is satisfied based on the cardiac EGM.

FIG. 7 is a graph illustrating a cardiac EGM 148 associated with an identified episode suspected to be asystole, and an example technique for determining whether an example false asystole detection criterion is satisfied based on cardiac EGM 148. In some examples, cardiac EGM 148 is a digitized segment of a cardiac EGM sensed by sensing circuitry 52 of IMD 10 via electrodes 16, and corresponds to a suspected asystole episode identified by processing circuitry 50 applying one or more asystole detection criteria to the cardiac EGM.

FIG. 7 illustrates cardiac depolarizations 150A-150H (in this example R-waves) identified by IMD 10, e.g., by comparing cardiac EGM 148 to an amplitude threshold, which may be automatically adjustable, as described herein. FIG. 7 also illustrates an asystole interval 152. Asystole interval 152 represents an interval of time between adjacent depolarizations 150F and 150G identified by IMD 10. As described herein, processing circuitry 50 may have determined that an asystole detection criterion was satisfied when asystole interval 152 reached a predetermined threshold amount of time. Based on the satisfaction of the asystole detection criterion, processing circuitry 50 may have stored cardiac EGM 148, including time periods before and after asystole interval 152, and indications of the detections (e.g., the timing) of depolarizations 150A-150H in storage device 52.

As described with reference to item 126 of FIG. 6, one false asystole detection criterion may include determining whether, using a reduced amplitude threshold 154, a threshold number of depolarizations are detected within cardiac EGM 148 during asystole interval 152. In the example illustrated by FIG. 7, processing circuitry 50 detects depolarizations 150I-150K during interval 152 by comparing cardiac EGM 148 to reduced amplitude threshold 154. The threshold number of depolarizations detected during interval 152 using threshold 154 needed to satisfy the reduced amplitude threshold criterion may be any integer greater than or equal to one, including two or three detected depolarizations.

In some examples, processing circuitry 50 determines reduced amplitude threshold 154 based on amplitudes of a predetermined number of depolarizations 150A-150F that precede asystole interval 152. In some examples, processing circuitry 50 determines the amplitudes of depolarizations 150A-150F by determining amplitudes of cardiac EGM 148 at samples corresponding to zero-crossings in a differential signal of cardiac EGM 148. In some examples, processing circuitry 50 determines a representative value of the amplitudes of depolarizations 150A-150F, e.g., a median or mean of the amplitudes, and determines reduced amplitude threshold 154 to be a predetermined portion, e.g., fraction or percentage, of the representative amplitude. As examples the predetermined portion may be 1/10, 1/8, 1/5, 1/3, or 1/2. Any number of preceding depolarizations may be used to determine threshold 154, such as two to eight preceding depolarizations, including six preceding depolarizations in some examples.

In one example, if the median amplitude of six preceding R-waves is 80 microvolts ($\mu V$), the reduced amplitude threshold 154 of $1/8^{th}$ of the median amplitude would be 10 $\mu V$. In such an example, processing circuitry 50 would determine the false asystole detection criterion was satisfied if there are 15 $\mu V$ signals in cardiac EGM 148 during interval 152. Applying reduced amplitude threshold 154 during asystole interval 152 may also obscure AV blocks with P-waves of 15 $\mu V$. However, application of this false asystole detection criterion based on satisfaction of an asystole detection count criterion (122 of FIG. 6), and the low probability that this false asystole detection criterion will be satisfied in by cardiac EGMs with relatively high R-wave amplitudes, reduces the likelihood of incorrect classification of the episode.

Figure 8:
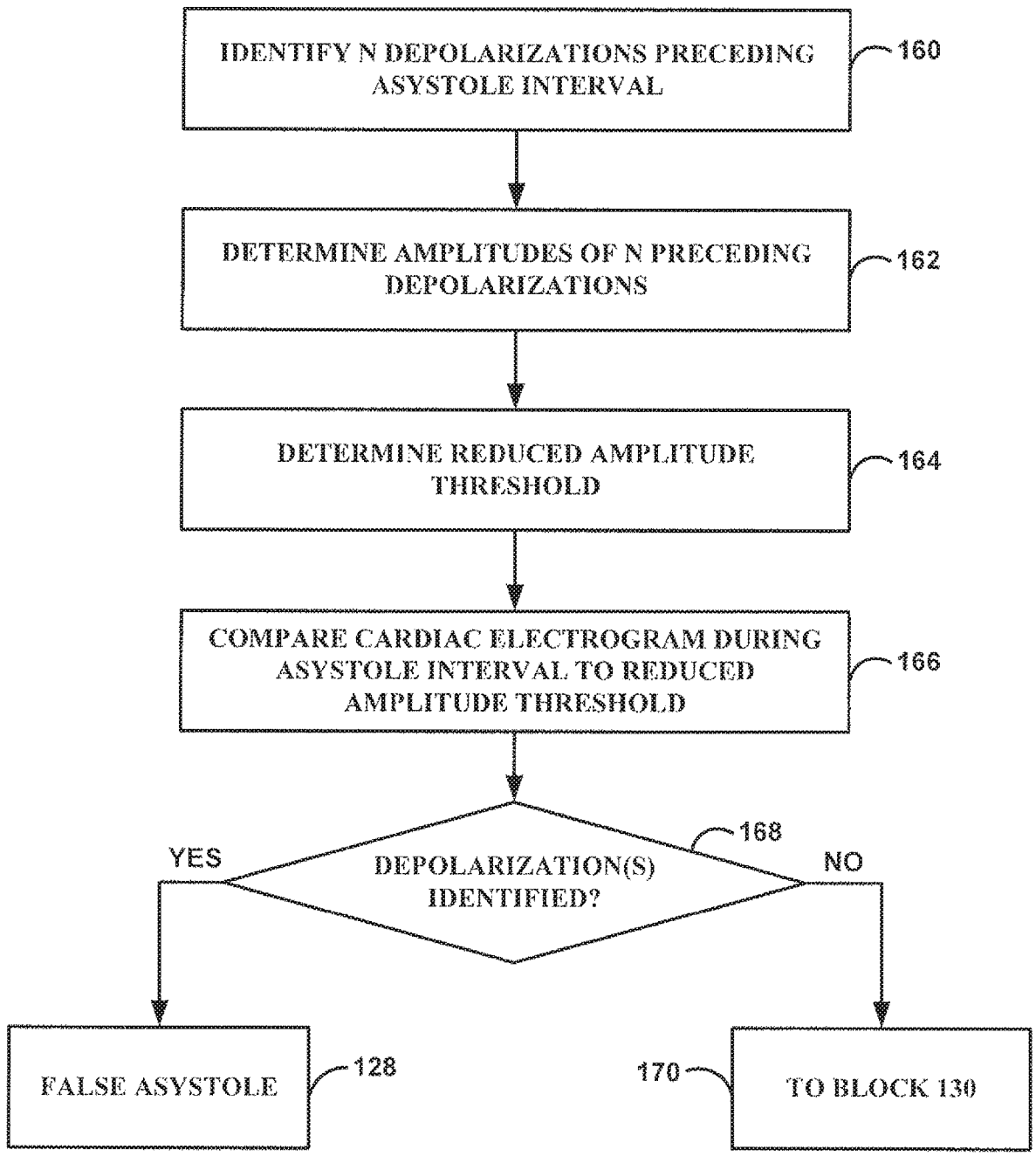
FIG. 8 is a flow diagram illustrating an example operation for determining whether an example false asystole criterion that includes a reduced amplitude threshold for depolarization detection is satisfied.

FIG. 8 is a flow diagram illustrating an example operation for determining whether an example false asystole criterion that includes a reduced amplitude threshold for depolarization detection is satisfied, e.g., corresponding to item 126 in FIG. 6. The example operation of FIG. 8 is described with reference to the cardiac EGM 148 and other data illustrated in FIG. 7.

According to the illustrated example of FIG. 8, processing circuitry 50 of IMD 10 identifies a predetermined number "N" of the depolarizations 150 preceding an asystole interval 152, e.g., the most recent N depolarizations before the asystole interval (160). Processing circuitry 50 determines the amplitudes of the N preceding depolarizations 150 (162). Processing circuitry 50 determines a reduced amplitude threshold 154 based on the amplitudes of the N preceding depolarizations 150, e.g., based on a predetermined fraction or other portion of a median or other representative value of the determined amplitudes of the N preceding depolarizations 150 (164).

Processing circuitry 50 compares the reduced amplitude threshold 154 to the cardiac EGM 148 within asystole interval 152, e.g., the portion of cardiac EGM 148 within the entire asystole interval or within a portion of the asystole interval (166). Processing circuitry 50 determines whether a threshold number of depolarizations 150 are identified within asystole interval 152 based on the comparison, e.g., based on cardiac EGM 148 being equal to or greater than reduced amplitude threshold 154 within the asystole interval (168). As examples, the threshold number of depolarizations may be one, two, or three depolarizations. Based on detecting the threshold number of depolarizations (YES of 168), processing circuitry 50 may determine that the suspected asystole episode is a false asystole (128). Based on not detecting the threshold number of depolarizations (NO of 168), processing circuitry 50 may proceed to application of another false asystole detection criterion, such as a decaying noise criterion described with reference to block 130 of FIG. 6 (170).

Figure 9:
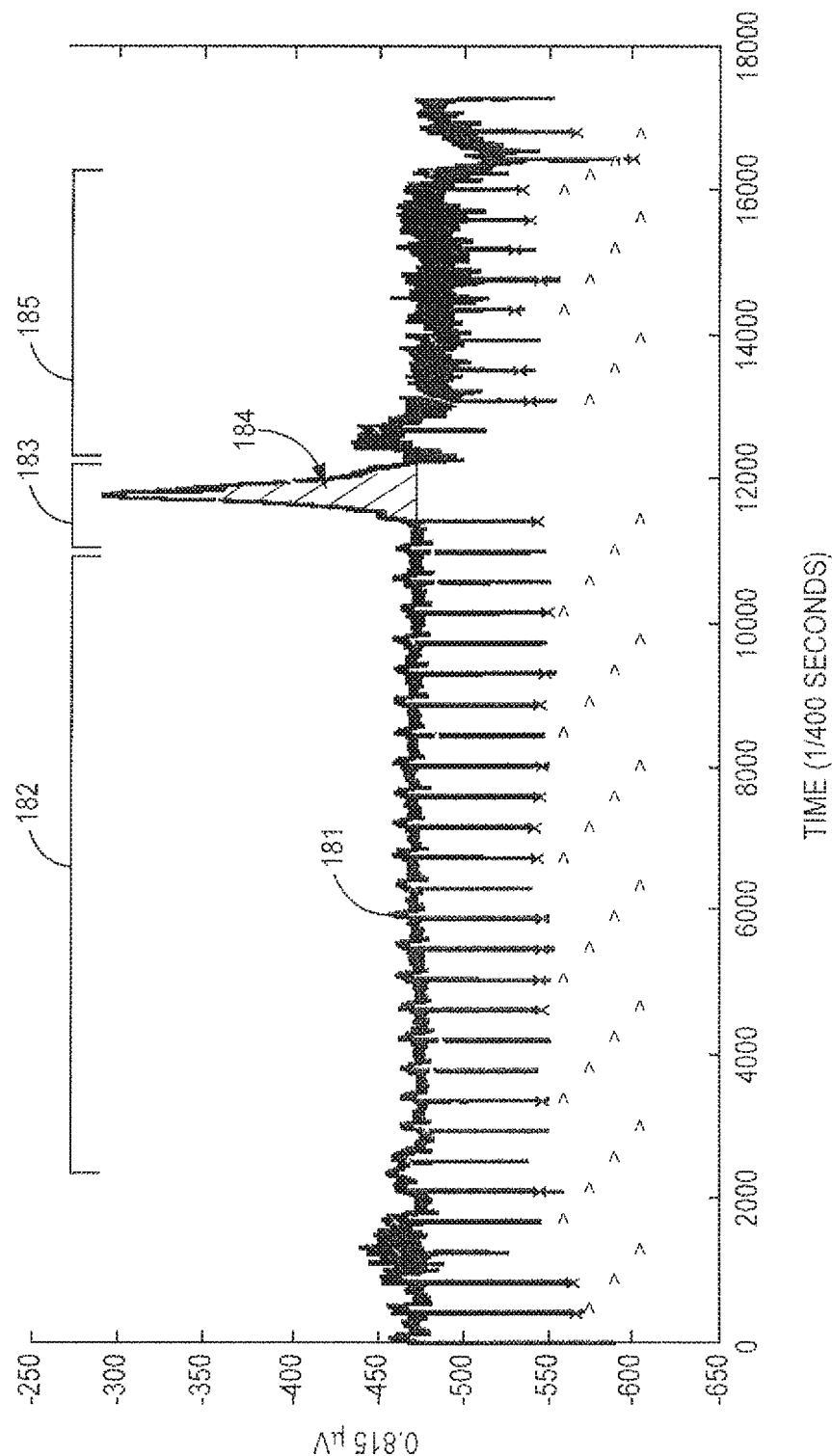
FIG. 9 is a graph illustrating a cardiac EGM that includes decaying noise.

FIG. 9 is a graph illustrating a cardiac EGM 181 that includes decaying noise. Cardiac EGM 181 may be a digitized cardiac EGM segment included as episode data for a suspected asystole episode.

Over the time span generally indicated by bracket 182, cardiac EGM 181 includes a somewhat consistent pattern of peaks and variations in amplitude that is repeated at a relatively consistent interval in time. During the time span generally indicated by bracket 183, cardiac EGM 181 does not continue to provide the consistent pattern previously provided during the time span indicated by bracket 182, but instead provides a large amplitude spike 184 having an amplitude and a duration that is much larger than any of the peaks provided in cardiac EGM 181 during the time span indicated by bracket 182.

Following the amplitude spike 184, and during the time span generally indicated by bracket 185, cardiac EGM 181 includes a larger variation in the amplitude of the signal, and may include more negative peaks and/or a lower overall average or median amplitude value compared to these same parameters if measured over the time span indicated by bracket 182. In some examples of a false asystole detection criterion, processing circuitry 50 may analyze amplitude spike 184 and/or the variations illustrated during the time span indicated by bracket 185 following the amplitude spike 184 to determine if these portions of cardiac EGM 181 are representative of a noise signal, e.g., decaying noise.

Figure 10:
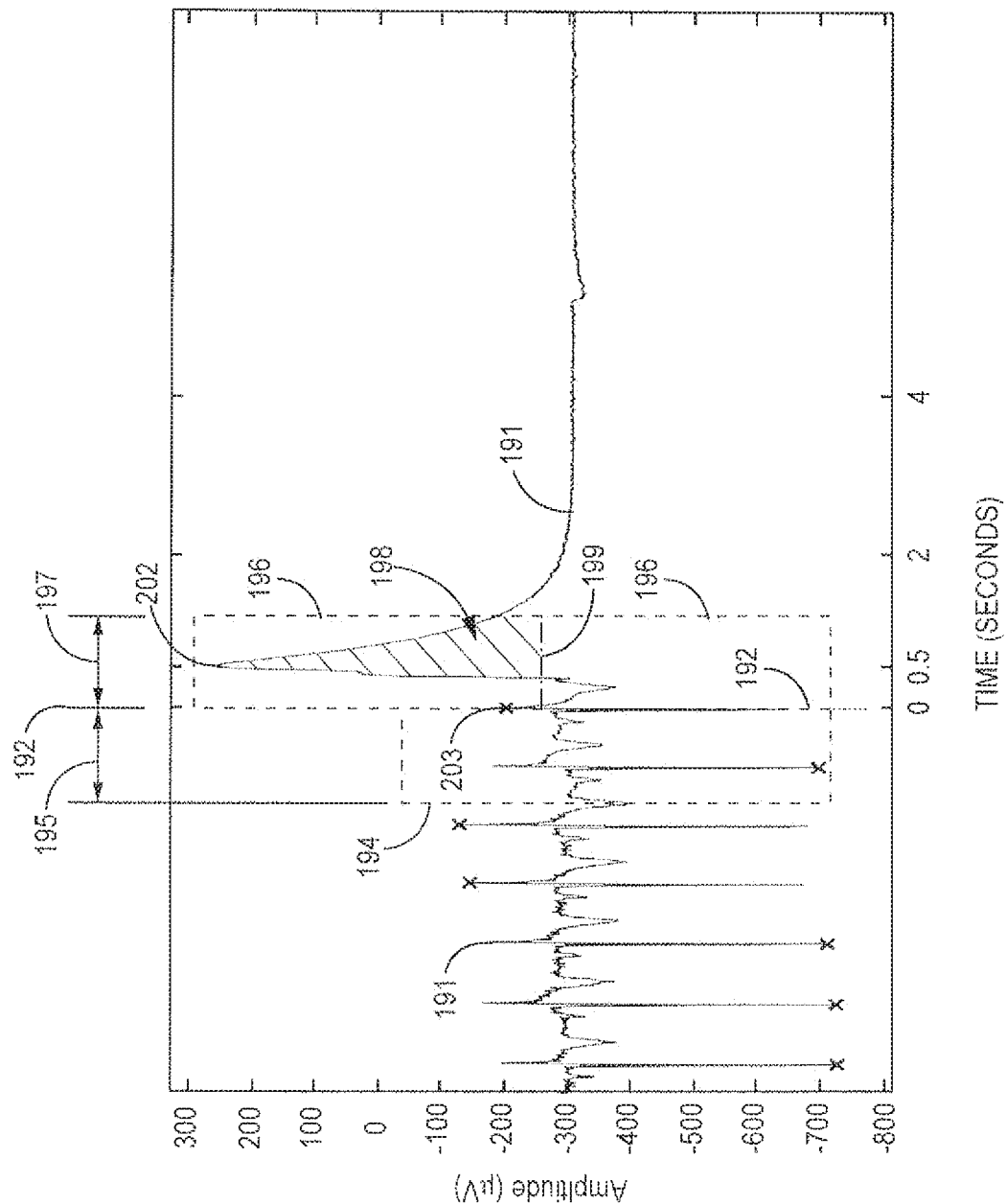
FIG. 10 is a graph illustrating a cardiac EGM that includes decaying noise and an example technique for determining whether an example false asystole detection criterion is satisfied based on the cardiac EGM.

FIG. 10 is a graph illustrating a cardiac EGM 191 that includes decaying noise and an example technique for determining whether an example false asystole detection criterion is satisfied based on the cardiac EGM. Cardiac EGM 191 may be a digitized cardiac EGM segment included by IMD 10 as episode data for a suspected asystole episode, e.g., based on processing circuitry 50 of IMD 10 determining that an asystole detection criterion was satisfied.

As shown in FIG. 10, cardiac EGM 191 includes an amplitude spike 202 in the portion of cardiac EGM 191 following the time indicated as "0" (zero) seconds. Using a set of detection windows, for example as illustratively represented by detection windows 194 and 196 in the example of FIG. 10, processing circuitry 50 may analyze one or more portions of cardiac EGM 191 to determine if cardiac EGM 191 includes a noise signal, such as the amplitude spike 202 or other decaying noise.

In various examples, analyzing cardiac EGM 191 to determine if a noise signal is present includes determining a sample time 192 as a basis for setting detection windows 194 and 196. In some examples, determining sample time 192 comprises setting the sample time equal to a time where a depolarization 203, e.g., R-wave, has been detected within cardiac EGM 191. Depolarization 203 may be a most recent depolarization preceding an asystole interval 152 (FIG. 7), in some examples.

Once processing circuitry 50 selects a sample time 192, processing circuitry 50 may set a baseline window 194 so that the baseline window includes a time span 195 extending from sample time 192 and for some amount of time prior to sample time 192. The width of time span 195 is not limited to any particular time span, and in some examples may be a time span in a range of 0.5 to 5 seconds. In the example of FIG. 10, baseline window 194 extends from sample time 192 and comprises an illustrative time span 195 of approximately 1 second, extending to include the portion of cardiac EGM 191 ranging from sample time 192 to a time up to one second prior to sample time 192.

In various examples, processing circuitry 50 determines a baseline amplitude value 199 based on sample time 192 and baseline window 194. Processing circuitry 50 may calculate the value for baseline amplitude 199 by determining the amplitudes of samples of cardiac EGM 191 that fall within baseline window 194, and determining baseline amplitude 199 based on these determined amplitude values. In some examples, the value for baseline amplitude 199 may be a mean or median of the amplitude values of cardiac EGM 191 during baseline window 194.

Processing circuitry 50 also sets a measurement window 196 to include a time span 197 extending from sample time 192 and for some amount of time following sample time 192. Time span 197 is not limited to any particular duration, and in some examples may be in a range of 0.5 to 5 seconds. In the example of FIG. 10, time span is approximately 1 second in duration, including the portion of cardiac EGM 191 ranging from sample time 192 to a time up to one second subsequent to sample time 192. In various examples, the width of time span 197 for the measurement window 196 is equal to or different then the width of time span 195 set for the baseline window 194. In examples in which depolarization 203 is a most recent depolarization preceding an asystole interval 152, measurement window 196 includes at least a portion of the asystole interval.

Processing circuitry 50 may determine amplitude values of samples of cardiac EGM 191 within measurement window 196. Processing circuitry 50 may determine an area-under-the-curve value for the portion of cardiac EGM 191 based on these sampled amplitude values within measurement window 196 and baseline amplitude value 199 determined based on baseline window 194.

For example, processing circuitry 50 may determine a set of difference values between the amplitude values of cardiac EGM 191 falling within the measurement window 196 and baseline amplitude value 199. In some examples, processing circuitry 50 determines an area-under-the-curve value by calculating an area 198 that is included below a portion of cardiac EGM 191 that falls within measurement window 196 and is above baseline amplitude value 199. Calculation of the area-under-the-curve value is not limited to any particular technique for calculating this area, and may include any technique for calculating an area under a curve, as would be understood by one of ordinary skill in the art. Once an area-under-the-curve value has been calculated for area 198, processing circuitry 50 may compare the area-under-the-curve value to a noise signal threshold value. In some examples, if the area-under-the-curve value exceeds or is equal to the noise signal threshold value, processing circuitry 50 determines that a noise signal has been detected within cardiac EGM 191 and that a false asystole detection criterion is satisfied.

Although baseline window 194 extends back in time and measurement window 196 extends forward in time from the most recent preceding depolarization 203 in the example of FIG. 10, processing circuitry 50 may set baseline window 194 and measurement window 196 with other time relationships to depolarization 203. For example, processing circuitry 50 may set baseline window 194 to extend forward in time from depolarization 203, and measurement window 196 to extend forward in time from an end of baseline window 194. In such examples, baseline window 194 may correspond to a period after detection of depolarization 203 during which IMD 10 is prevented from detecting subsequent depolarizations, referred to as a blanking period. In such examples, measurement window 196 may have a greater duration than baseline window 194, e.g., to capture an expected duration of amplitude spike 202. In some examples, baseline window 194 and measurement window 196 need not be consecutive or contiguous.

Generally, P-waves are relatively narrower and/or more evenly distributed above and below the baseline amplitude, and therefore have smaller area-under-the-curve measurements, then decaying, e.g., exponentially decaying, noise signals. Consequently, area-under-the-curve measurement may be an effective discriminator between P-waves occurring during true asystole and decaying noise that resulted in false asystole detection.

Figure 11:
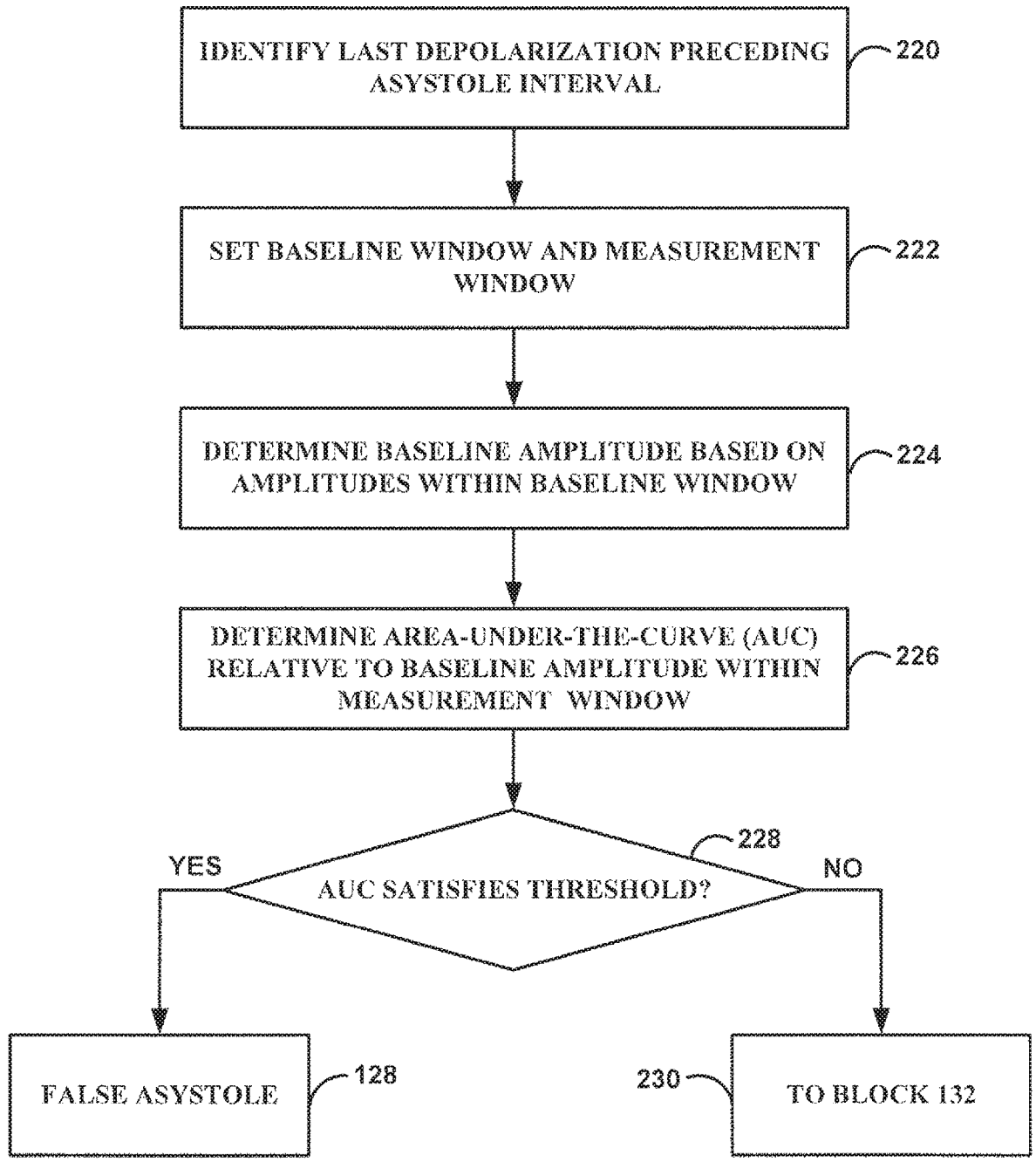
FIG. 11 is a flow diagram illustrating an example operation for determining whether an example false asystole criterion for detecting decaying noise is satisfied.

FIG. 11 is a flow diagram illustrating an example operation for determining whether an example false asystole criterion for detecting decaying noise is satisfied, e.g., corresponding to item 130 in FIG. 6. The example operation of FIG. 11 is described with reference to the cardiac EGM 148 and other data illustrated in FIG. 7, and cardiac EGM 191 and other data illustrated in FIG. 10.

According to the example of FIG. 11, processing circuitry 50 identifies a last depolarization 203 preceding an asystole interval 152 (220). Processing circuitry 50 further sets baseline window 194 and measurement window 196 based on the time of last depolarization 203 (222). Processing circuitry 50 determines baseline amplitude 199 based on amplitudes of cardiac EGM 191 within baseline window 194, e.g., as a mean or median of the amplitudes within baseline window 194 (224).

Processing circuitry 50 further determines an area-under-the-curve measurement for the portion of cardiac EGM 191 within measurement window 196 relative to baseline amplitude 199 (226). For example, processing circuitry 50 may determine the area-under-the curve measurement based on a sum of the differences between the amplitudes of samples of cardiac EGM 191 within measurement window 196 and the baseline amplitude 199. Any known techniques for area-under-the-curve measurement may be employed.

Processing circuitry 50 determines whether the area-under-the-curve measurement satisfies a threshold, e.g., equal to or greater than the threshold (228). Based on the area-under-the-curve measurement satisfying the threshold (YES of 228), processing circuitry 50 may determine that the suspected asystole episode is a false asystole (128). Based on the area-under-the-curve measurement not satisfying threshold (NO of 228), processing circuitry 50 may proceed to application of another false asystole detection criterion, such as a preceding depolarization variability criterion as described with reference to block 132 of FIG. 6 (170).

Figure 12:
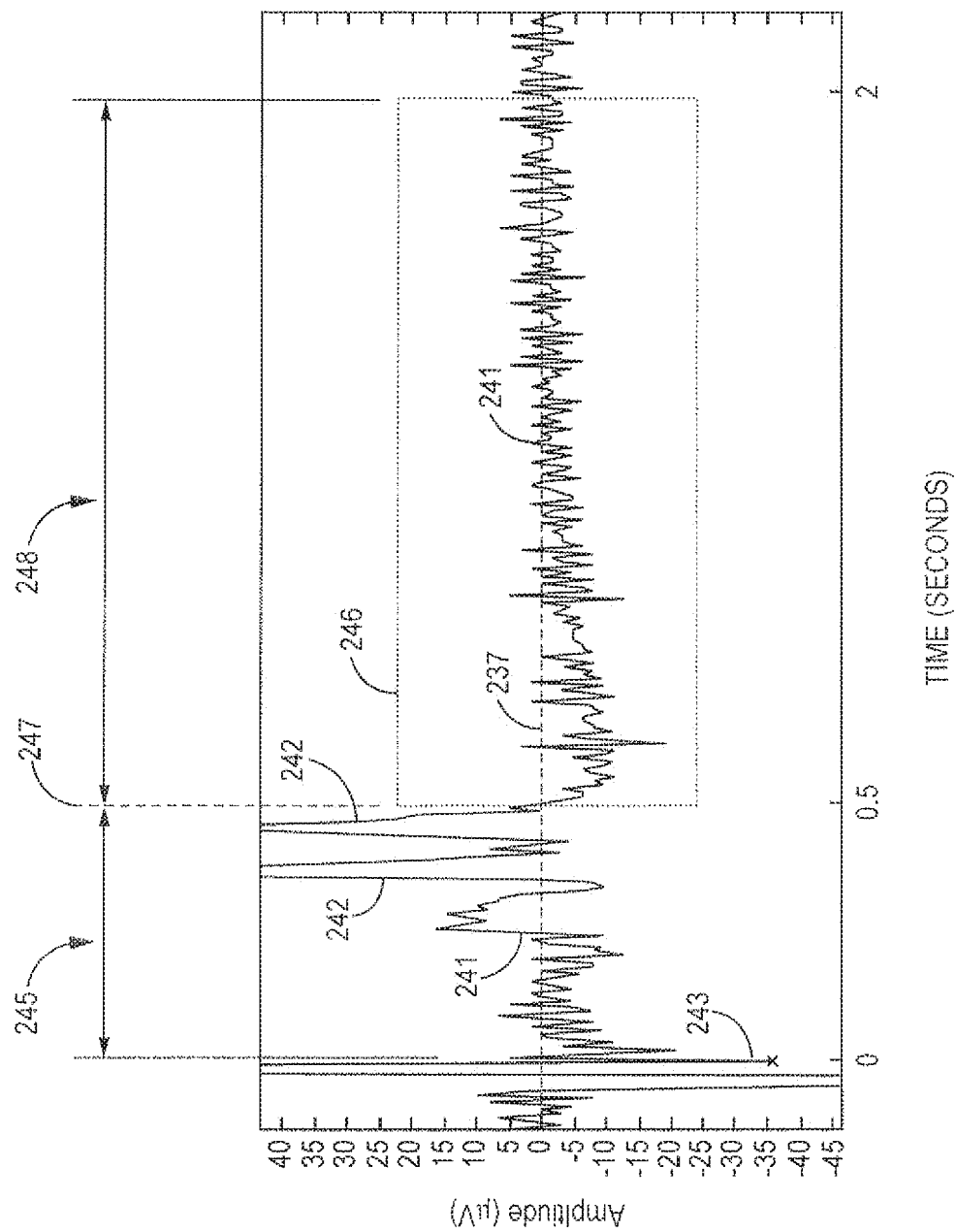
FIG. 12 is a graph illustrating a differential signal of a cardiac EGM that includes decaying noise and an example technique for determining whether an example false asystole detection criterion is satisfied based on the cardiac EGM.

FIG. 12 is a graph illustrating a differential signal 241 of a cardiac EGM that includes decaying noise and an example technique for determining whether an example false asystole detection criterion is satisfied based on the cardiac EGM. Processing circuitry 50 of IMD 10 may determine differential signal 241 based on a digitized cardiac EGM segment included by IMD 10 as episode data for a suspected asystole episode, e.g., based on processing circuitry 50 determining that an asystole detection criterion was satisfied. In some examples, processing circuitry 50 determines the value of each sample "y" of differential signal 241 by taking an amplitude value for the corresponding sample "y" of the cardiac EGM, and subtracting from that amplitude value the amplitude value of the cardiac EGM at sample "y-n", wherein n is a predetermined number of samples.

As shown in FIG. 12, some of the values of differential signal 241 fall below a "zero" value line 237, and some of the signal values within differential signal 241 fall above the "zero" value line 237. A noise signal in the cardiac EGM, such as the amplitude spike 202 as illustrated in FIG. 10, may result in a differential signal having one or more spikes, such as spikes 242 in differential signal 241, followed by a gradual return of differential signal 241 to zero value line 237.

Processing circuitry 50 may set a measurement window 246 based on the detection of an event, such as an R-wave of other depolarization 243 in the cardiac EGM. In the illustrated example, a time span 245 begins at the time of detection of depolarization 243. In the example of FIG. 12, time span 245 extends for a time period of 0.5 seconds. The time period included within time span 245 is not limited to any particular time span, and may range from 0.2 to 1 second in some examples. In some examples, time span 245 may correspond to a period after detection of depolarization 243 during which IMD 10 is prevented from detecting subsequent depolarizations, referred to as a blanking period.

Measurement window 246 begins at the time of expiration of time span 245, illustrated by vertical dashed line 247, and extends over time span 248, ending at the expiration of time span 248. In the example of FIG. 12, time span 248 extends for a time period of 1.5 seconds. The time period included in time span 248 is not limited to any particular time span, and may range from one to five seconds in some examples.

Processing circuitry 50 determines a sign, i.e., positive above zero line 237, negative below zero line 237, or on the zero line for the samples of differential signal 241 within measurement window 246. Processing circuitry 50 determines a count of one or more of the signs, and determines whether the count satisfies, e.g., equals, exceeds, or is below, a threshold. The count may take the form of a percentage or fraction of the total number of samples considered. In general, when decaying noise is present in the cardiac EGM, the signs of differential signal 241 within measurement window 246 will be unbalanced, e.g., more signs are negative in the example of FIG. 12. Although negative signs may be counted or quantified in some examples, other examples may include counting or quantifying a number of positive sample values, a number of non-negative sample values (e.g., a count of zero sample values plus positive sample values) or a number of non-positive sample values (e.g., a count of zero sample values plus negative sample values).

Using an imbalance of the signs of a differential signal within a measurement window following last depolarization to detect the presence of decaying noise may involve easier calculations for processing circuitry 50 of IMD 10 then calculating an area-under-the-curve to detect the decaying noise. Further, P-waves or thermal noise occurring during an asystole interval during a true asystole will have a substantially equal distribution of signs of the differential signal within the measurement window (occurring during the asystole interval) while exponential or other decaying noise may have more than 70% of samples with a comment, e.g., negative, sign.

Figure 13:
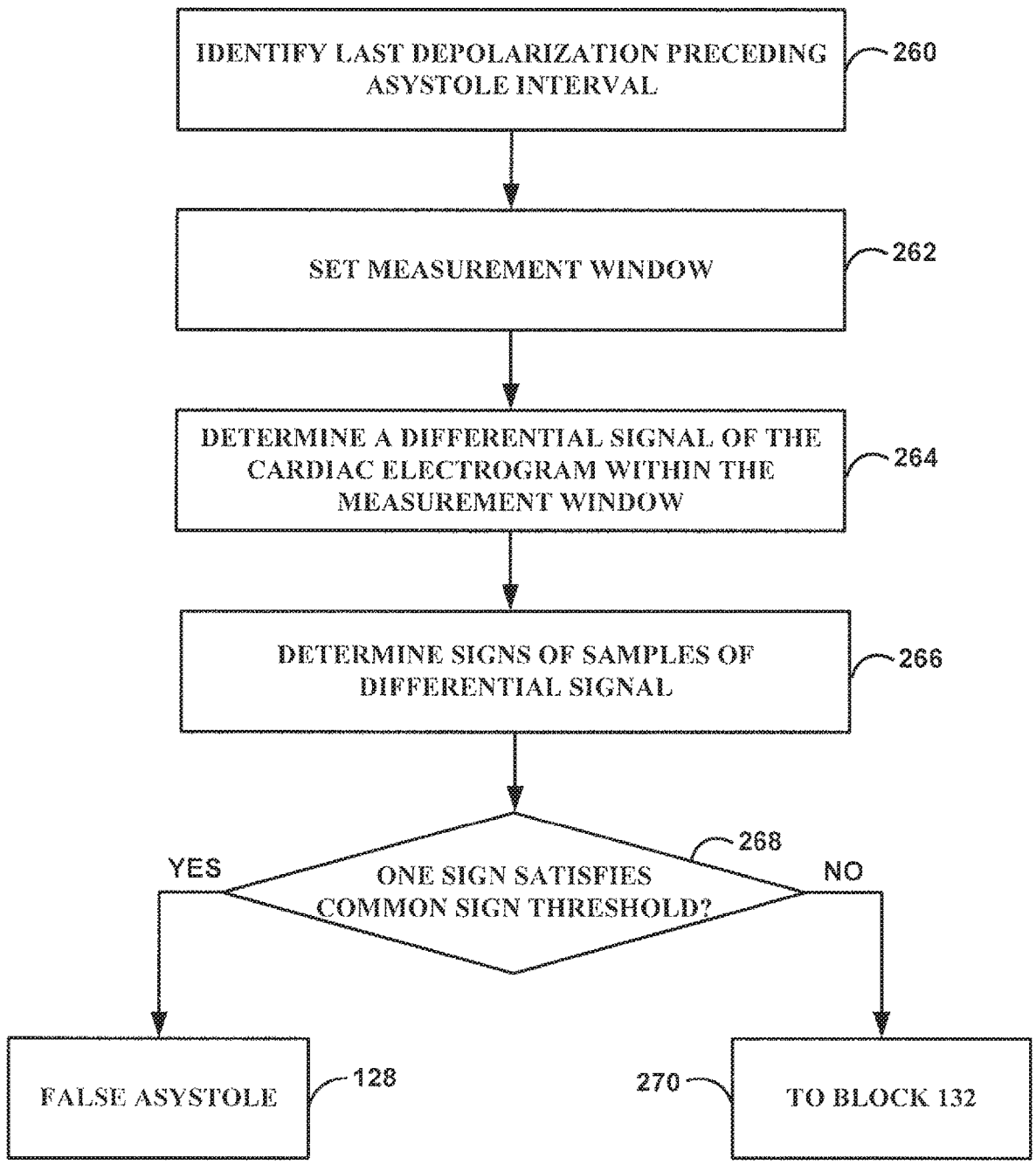
FIG. 13 is a flow diagram illustrating another example operation for determining whether an example false asystole criterion for detecting decaying noise is satisfied.

FIG. 13 is a flow diagram illustrating another example operation for determining whether an example false asystole criterion for detecting decaying noise is satisfied. The example operation of FIG. 13 is described with reference to the cardiac differential signal 241 and other data illustrated in FIG. 12.

According to the example of FIG. 13, processing circuitry 50 identifies a last depolarization 243 preceding an asystole interval, e.g., asystole interval 152 in FIG. 7 (260). Processing circuitry further sets a measurement window 246 that begins a time period 245 after the last depolarization (262), and determines a differential signal 241 within the measurement window 246 (264). Processing circuitry 50 further determines the signs of samples of differential signal 241 within measurement window 246 and, for at least one of the signs, counts or otherwise quantifies the number of samples having the sign (266).

Processing circuitry 50 determines whether the count of one of the signs satisfies a common sign threshold, e.g., is equal to or greater than the threshold (268). Based on the common sign threshold being satisfied (YES of 268), processing circuitry 50 may determine that the suspected asystole episode is a false asystole (128). Based on the common sign threshold not being satisfied (NO of 268), processing circuitry 50 may proceed to application of another false asystole detection criterion, such as a preceding depolarization variability criterion as described with reference to block 132 of FIG. 6 (270).

Figure 14:
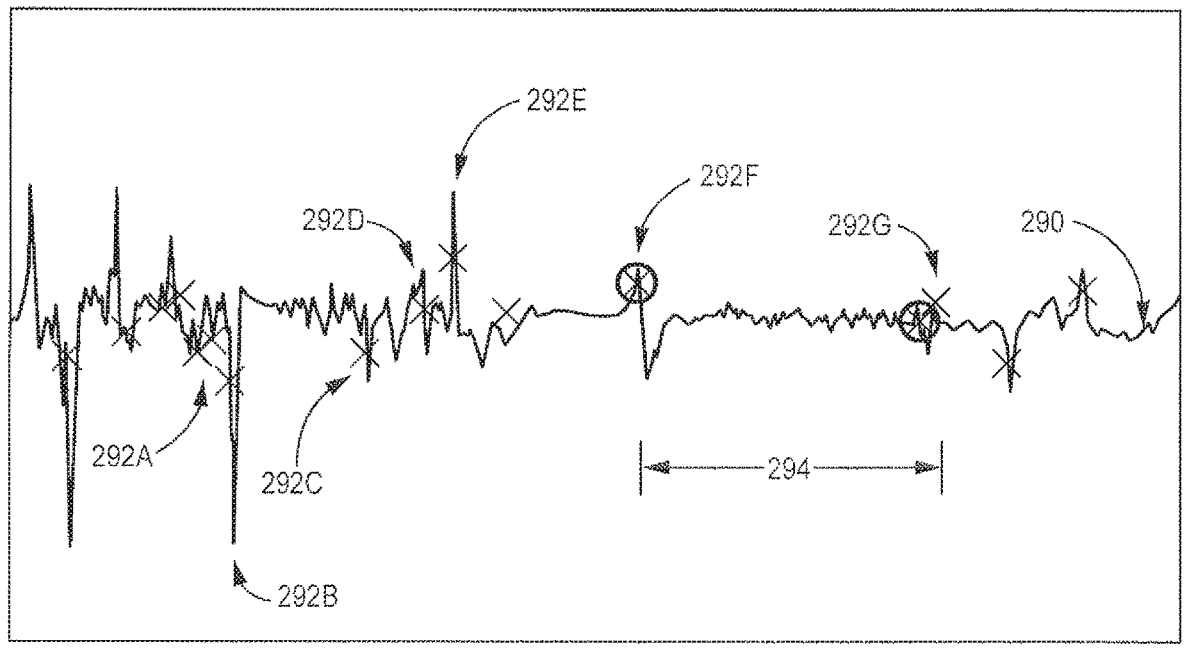
FIG. 14 is a graph illustrating a cardiac EGM associated with an identified asystole episode and an example technique for determining whether another example false asystole detection criterion is satisfied based on the cardiac EGM.

FIG. 14 is a graph illustrating a cardiac EGM 290 associated with an identified asystole episode and an example technique for determining whether another example false asystole detection criterion is satisfied based on the cardiac EGM. Cardiac EGM 290 may be a digitized cardiac EGM segment included by IMD 10 as episode data for a suspected asystole episode, e.g., based on processing circuitry 50 of IMD 10 determining that an asystole detection criterion was satisfied.

FIG. 14 illustrates cardiac depolarizations 292A-292G (in this example R-waves) identified by IMD 10, e.g., by comparing cardiac EGM 290 to an amplitude threshold, which may be automatically adjustable, as described herein. FIG. 14 also illustrates an asystole interval 294. Asystole interval 294 represents an interval of time between adjacent (in time) depolarizations 292F and 292G identified by IMD 10. As described herein, processing circuitry 50 may have determined that an asystole detection criterion was satisfied when asystole interval 294 reached a predetermined threshold amount of time. Based on the satisfaction of the asystole detection criterion, processing circuitry may have stored cardiac EGM 290, including time periods before and after asystole interval 294, and indications of the detections (e.g., the timing) of depolarizations 292A-292G (collectively, "depolarizations 292") in storage device 52.

As described with reference to item 132 of FIG. 6, one false asystole detection criterion may include determining whether a variability of N depolarizations 292 preceding asystole interval 294 satisfies a variability threshold. The number "N" of depolarizations preceding asystole interval 294 may be any integer greater than one, such as four, six, or eight. The N depolarizations 292 may, but need not, include the last depolarization 292F preceding asystole interval 294. For example, processing circuitry 50 may determine a variability of the six depolarizations 292A-292F preceding asystole interval 292.

The variability may be of amplitudes or other characteristics of the depolarizations 292. Processing circuitry 50 may use any known technique for measuring or otherwise characterizing the variability of a plurality of values in order to determine the variability of the preceding depolarizations 292. In some examples, processing circuitry 50 compares, e.g., determines a difference between, a maximum amplitude and a median amplitude of the preceding depolarizations. In such examples, processing circuitry 50 may determine whether the difference or other comparison satisfies, e.g., exceeds, a predetermined threshold.

Electrical noise can cause false asystole detection. In some examples, the cardiac EGM for an asystole episode falsely detected due to electrical noise looks like a flat line added with random peaks ranging from 40 uV to 2000 uV. A true cardiac EGM would likely not include such a wide range in R-wave amplitudes in few seconds. Variability of preceding depolarizations, e.g., difference between the maximum and median, may be very sensitive and specific to false asystole detection caused by electric noise. Although such a criterion might wrongly reject a true asystole detection if electrical noise happens to occur just prior to a true asystole detection, this confluence is unlikely to occur, particularly in IMDs with asystole detection frequencies below an asystole count detection threshold (122 of FIG. 6).

Figure 15:
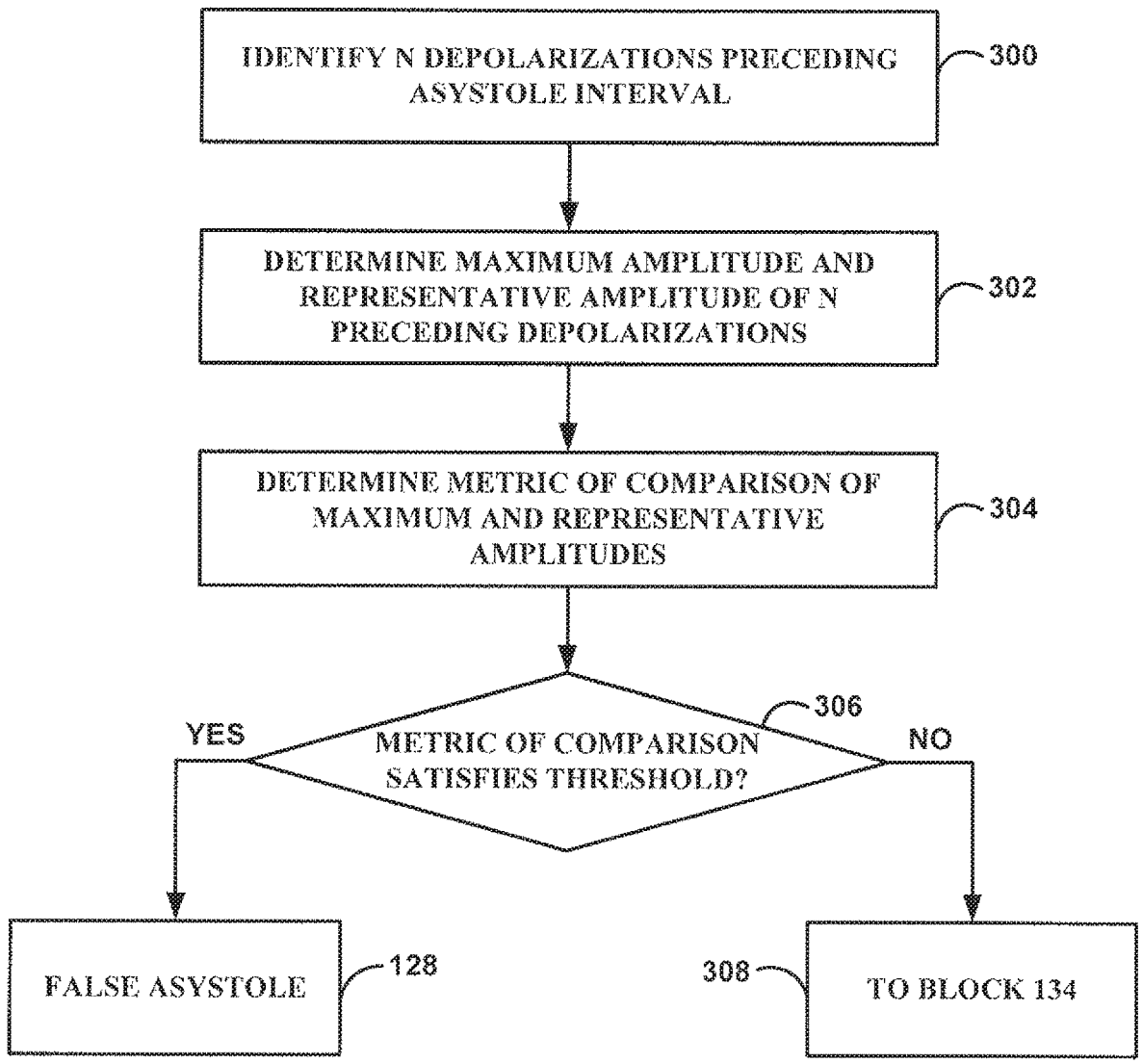
FIG. 15 is a flow diagram illustrating another example operation for determining whether an example false asystole criterion is satisfied.

FIG. 15 is a flow diagram illustrating another example operation for determining whether an example false asystole criterion is satisfied. The example operation of FIG. 15 is described with reference to the cardiac EGM 290 and other data illustrated in FIG. 14.

According to the example of FIG. 15, processing circuitry 50 identifies N depolarizations 292 preceding asystole interval 294 (300). Processing circuitry 50 determines a variability of the N preceding depolarizations 292. For example, processing circuitry 50 may determine amplitudes of the N preceding depolarizations 292, determine a maximum amplitude of the N preceding depolarizations 292, and determine a representative value of the amplitudes of the N preceding depolarizations 292, e.g., a median or mean of the amplitudes (302). Processing circuitry 50 further determines a metric of comparison between the maximum amplitude and the representative amplitude, such as a difference or ratio (304).

Processing circuitry 50 determines whether the metric of comparison satisfies the threshold, e.g., is equal to or greater than the threshold (306). Based on the metric of comparison satisfying the threshold (YES of 306), processing circuitry 50 may determine that the suspected asystole episode is a false asystole (128). Based on the metric of comparison not satisfying the threshold (NO of 306), processing circuitry 50 may proceed to application of another false asystole detection criterion, such as an energy pattern criterion as described with reference to block 134 of FIG. 6 (308).

Figure 16:
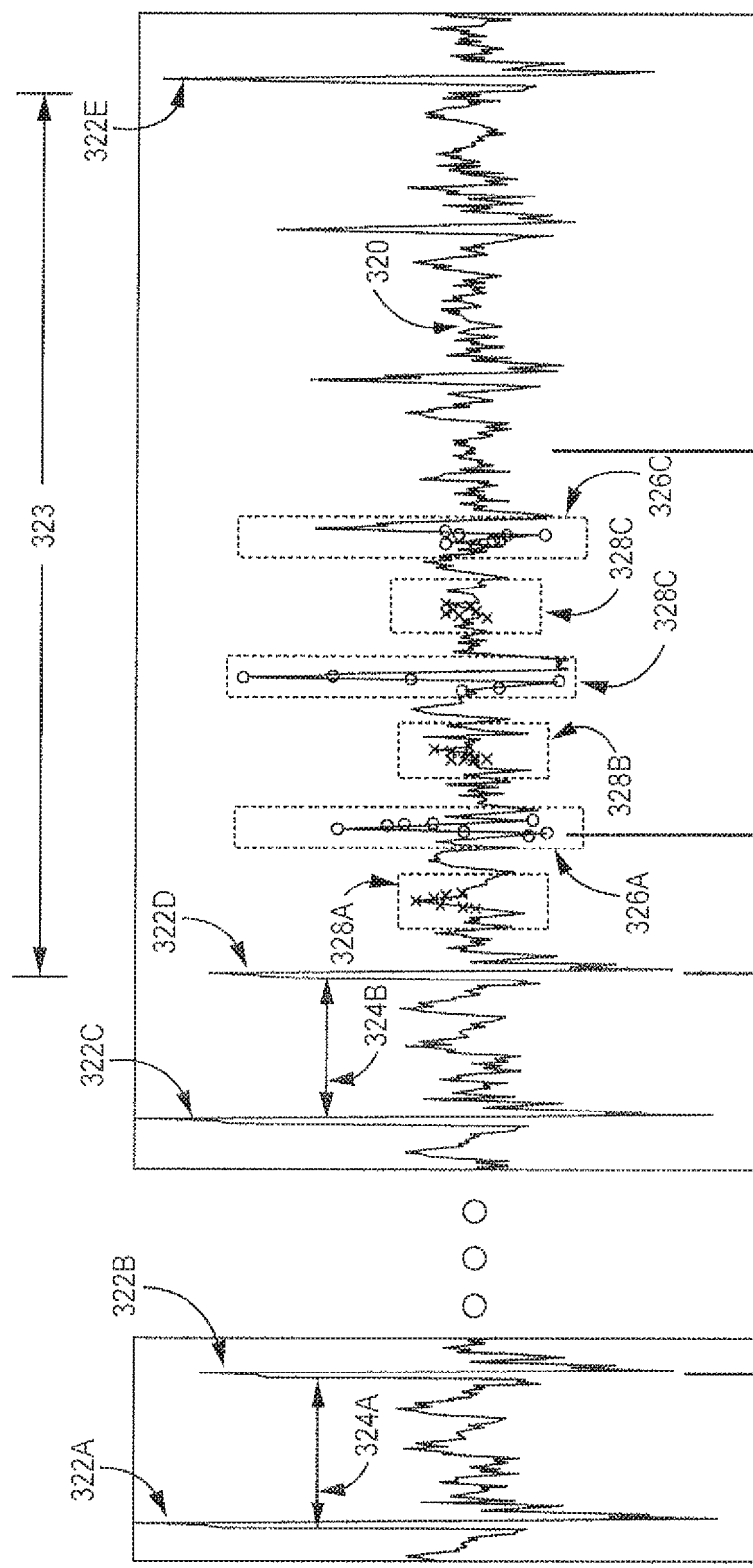
FIG. 16 is a graph illustrating a cardiac EGM associated with an identified asystole episode and an example technique for determining whether another example false asystole detection criterion is satisfied based on the cardiac EGM.

FIG. 16 is a graph illustrating a cardiac EGM 320 associated with an identified asystole episode and an example technique for determining whether another example false asystole detection criterion is satisfied based on the cardiac EGM. Cardiac EGM 320 may be a digitized cardiac EGM segment included by IMD 10 as episode data for a suspected asystole episode, e.g., based on processing circuitry 50 of IMD 10 determining that an asystole detection criterion was satisfied.

FIG. 16 illustrates cardiac depolarizations 322A-322E (in this example R-waves) identified by IMD 10, e.g., by comparing cardiac EGM 320 to an amplitude threshold, which may be automatically adjustable, as described herein. FIG. 16 also illustrates an asystole interval 323. Asystole interval 323 represents an interval of time between adjacent depolarizations 322D and 322E identified by IMD 10. As described herein, processing circuitry 50 may have determined that an asystole detection criterion was satisfied when asystole interval 323 reached a predetermined threshold amount of time. Based on the satisfaction of the asystole detection criterion, processing circuitry 50 may have stored cardiac EGM 320, including time periods before and after asystole interval 323, and indications of the detections (e.g., the timing) of depolarizations 322A-322E (collectively, "depolarizations 322") in storage device 52.

As described with reference to item 134 of FIG. 6, one false asystole detection criterion may include evaluating an energy pattern of cardiac EGM 320 during asystole interval 323. When a physician reviews a graphical representation of a cardiac EGM, such as cardiac EGM 320, to determine whether a suspected asystole is true or false, the physician may measure or estimates R-R intervals before asystole interval 323, and determine whether there are visible small peaks within asystole interval 323 that are in the same pace or in phase with, e.g., that would have similar R-R intervals to, the preceding R-R intervals. Such a pattern may indicate to the physician that the asystole detection was false and caused by, for example, a drop in R-wave amplitude. In contrast, small peaks within asystole interval 323 that are out of phase with the preceding R-R intervals might be P-waves during a true asystole caused by A-V block.

In some examples, processing circuitry 50 identifies N depolarizations 322 preceding asystole interval 323, e.g., N consecutive depolarizations 322 including the last depolarization 322D preceding asystole interval 323. Based on the N preceding depolarizations 322, processing circuitry 50 may determine N−1 intervals between the preceding depolarizations 322, including intervals 324A and 324B (collectively, "inter-depolarization intervals 324"). N may be any integer, such as seven or thirteen. Within asystole interval 323, processing circuitry 50 sets expected depolarization windows 326A-326C (collectively "expected depolarization windows 326") and expected inter-depolarization windows 328A-328C (collectively, "expected inter-depolarization windows 328") based on inter-depolarization intervals 324. Although three of each type of window are illustrated in the example of FIG. 16, other examples may employ more or fewer of each type of window, and/or different numbers of windows for the two types of windows In some examples, processing circuitry 50 determines a median or other representative value of inter-depolarization intervals 324. Processing circuitry 50 may set windows 326 and 328 within asystole interval 323 based on the representative value of inter-depolarization intervals 324. For example, processing circuitry 50 may set each of expected depolarization windows 326 to occur, e.g., be centered at a time that is, a different integer multiple of the representative interval after the last preceding depolarization 322D. In one such example, processing circuitry 50 may set expected depolarization window 326A to be the representative interval after depolarization 322D, expected depolarization window 326B to be two times the representative interval after depolarization 322D, and expected depolarization window 326C to be three times the representative interval after depolarization 322D. Processing circuitry 50 may set each of expected inter-depolarization windows 328 to occur, e.g., be centered at a time that is, a different non-integer, e.g., fractional, multiple of the representative interval after the last preceding depolarization 322D. In one such example, processing circuitry 50 may set expected inter-depolarization window 328A to be the one-half the representative interval after depolarization 322D, expected inter-depolarization window 328B to be one and one-half times the representative interval after depolarization 322D, and expected inter-depolarization window 328C to be two and one-half times the representative interval after depolarization 322D. The width of windows 326 and 328 may be set as a predetermined portion, e.g., fraction or percentage, or the representative interval, and the predetermined portion may be the same or different as between windows 326 and windows 328.

Processing circuitry 50 determines a first energy value for expected depolarization windows 326 and a second energy value for expected inter-depolarization windows 328. In some examples, processing circuitry 50 determines an energy value for each of windows 326 and windows 328, and then determines a first mean, median, or other representative energy value of the energy values of windows 326, and a second representative energy value of the energy values of windows 328. Processing circuitry 50 may employ any known technique for determining an energy of a signal within a window. In some examples, as an energy value for each of the windows 326 and 328, processing circuitry 50 determines a difference, ratio, or other metric of comparison between a maximum amplitude of cardiac EGM 320 and minimum amplitude of cardiac EGM 320 within the window.

Processing circuitry 50 further determines a difference, ratio, or other metric of comparison between the first representative energy value for the expected depolarization windows 326 and the second representative energy value for the expected inter-depolarization windows 328. Processing circuitry 50 determines whether the metric of comparison satisfies, e.g., is equal to or exceeds, a threshold. The first representative energy value being relatively high compared to the second energy level may indicate the presence of low amplitude depolarizations, e.g., R-waves, within asystole interval 323 that are in phase with the rhythm prior to asystole interval 323, and that the suspected asystole was a false asystole detection.

Figure 17:
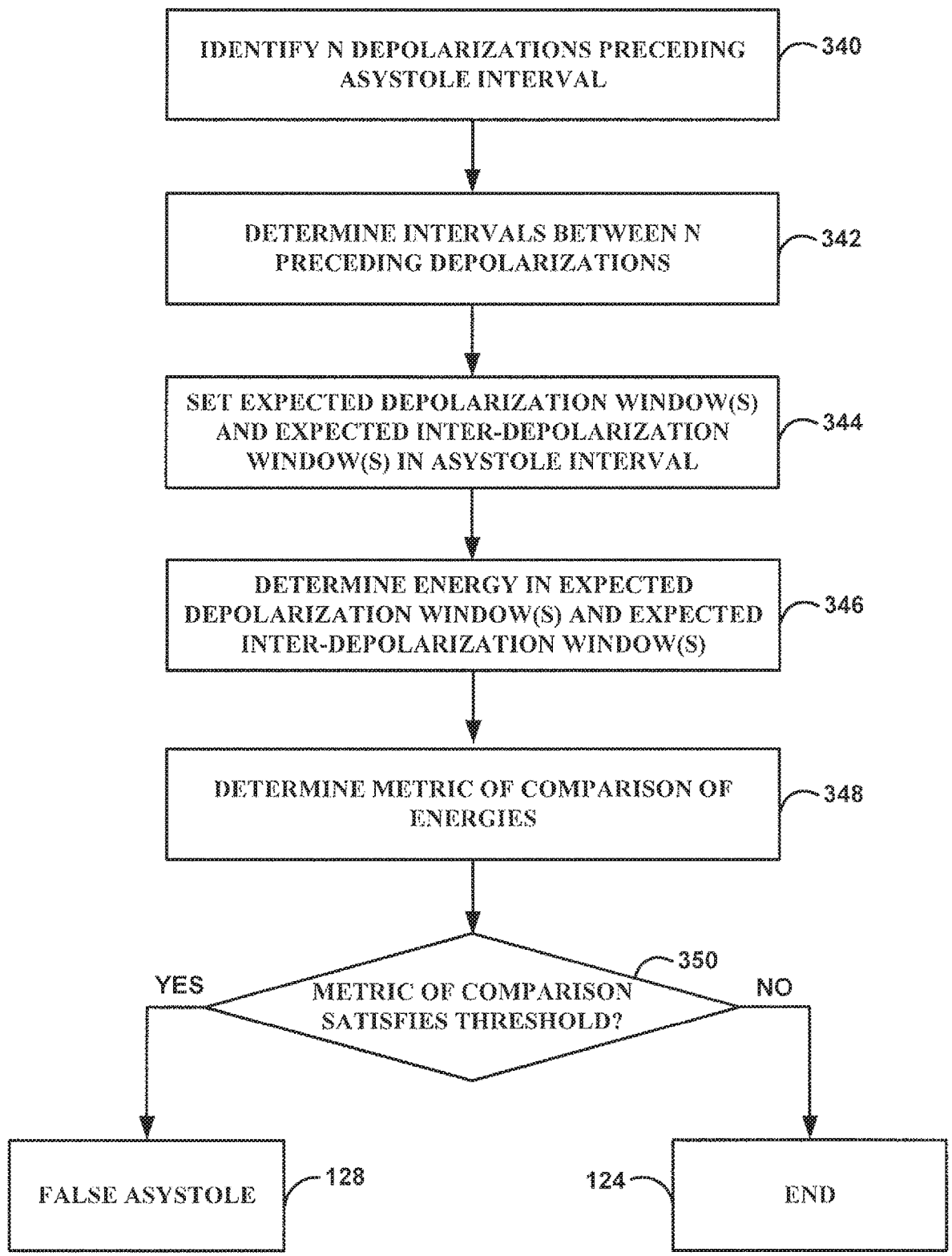
FIG. 17 is a flow diagram illustrating another example operation for determining whether an example false asystole criterion is satisfied.

FIG. 17 is a flow diagram illustrating another example operation for determining whether an example false asystole criterion is satisfied. The example operation of FIG. 17 is described with reference to the cardiac EGM 320 and other data illustrated in FIG. 16.

According to the example of FIG. 17, processing circuitry 50 identifies N depolarizations 322 preceding asystole interval 323 (340). Processing circuitry 50 determines intervals 324 between the N preceding depolarizations 322 (342). Processing circuitry 50 further sets expected depolarization windows 326 and expected inter-depolarization windows 328 within asystole interval 323 based on the intervals 324, e.g., based on integer and non-integer multiples, respectively, of a mean or median of intervals 124 (344).

Processing circuitry 50 determines respective energy values for expected depolarization windows 326 and expected inter-depolarization windows 328, e.g., a difference between a maximum amplitude and a minimum amplitude of cardiac EGM 320 within each window (346). Processing circuitry 50 further determines a metric of comparison between the energies of windows 326 and the energies of windows 328 (348). For example, processing circuitry 50 may determine a difference between a mean of the energies of windows 326 and a mean of the energies of windows 328.

Processing circuitry 50 determines whether the metric of comparison satisfies the threshold, e.g., is equal to or greater than the threshold (350). Based on the metric of comparison satisfying the threshold (YES of 350), processing circuitry 50 may determine that the suspected asystole episode is a false asystole (128). Based on the metric of comparison not satisfying the threshold (NO of 350), processing circuitry 50 may proceed to application of another false asystole detection criterion or, if there is not another false asystole detection criterion to apply, the operations of FIGS. 17 and 6 may end (124).

Figure 18A:
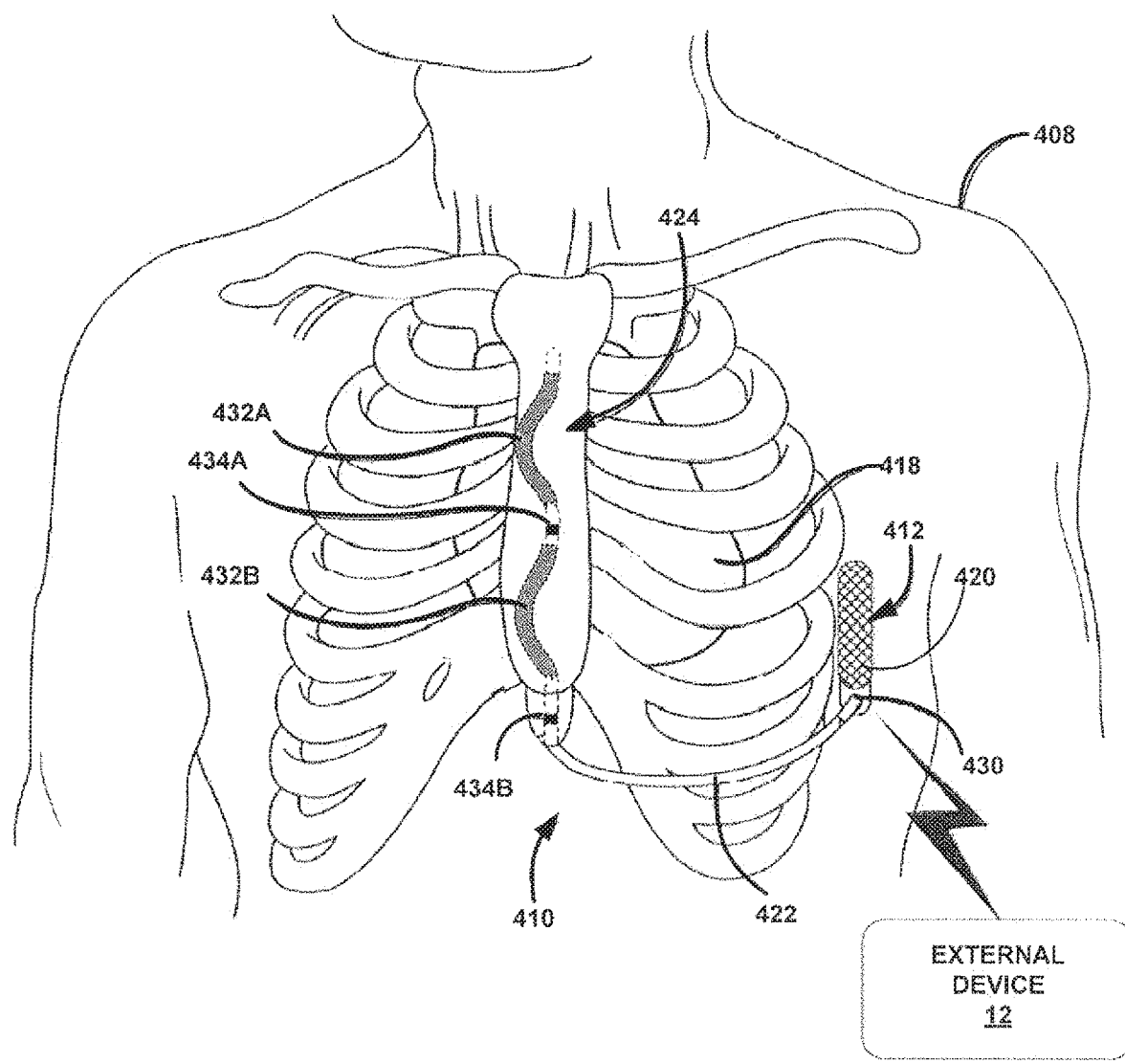
FIG. 18A is a conceptual drawing illustrating a front view of a patient with another example medical system.
Figure 18B:
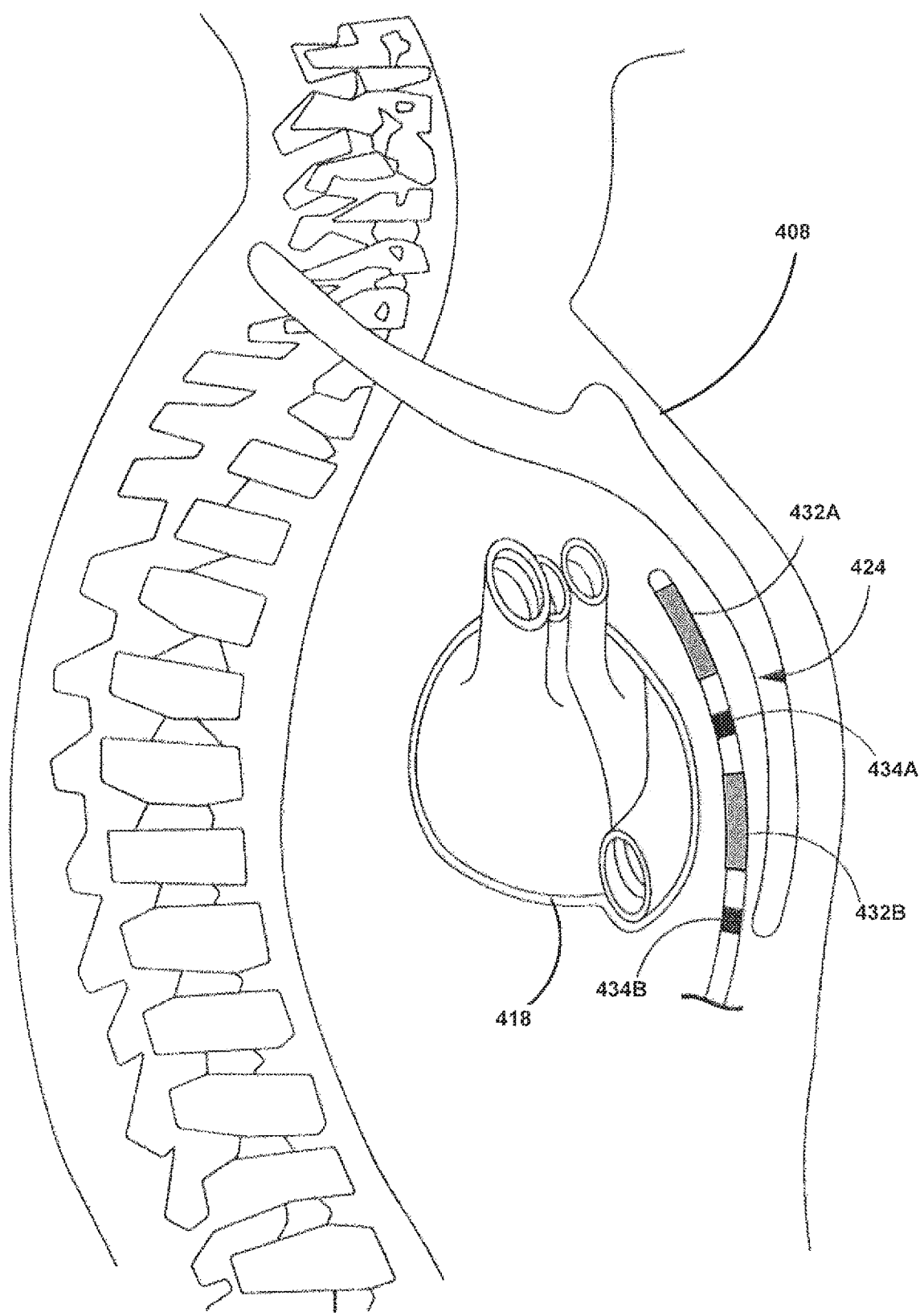
FIG. 18B is a conceptual drawing illustrating a side view of the patient with the example medical system of FIG. 18A.
Figure 18C:
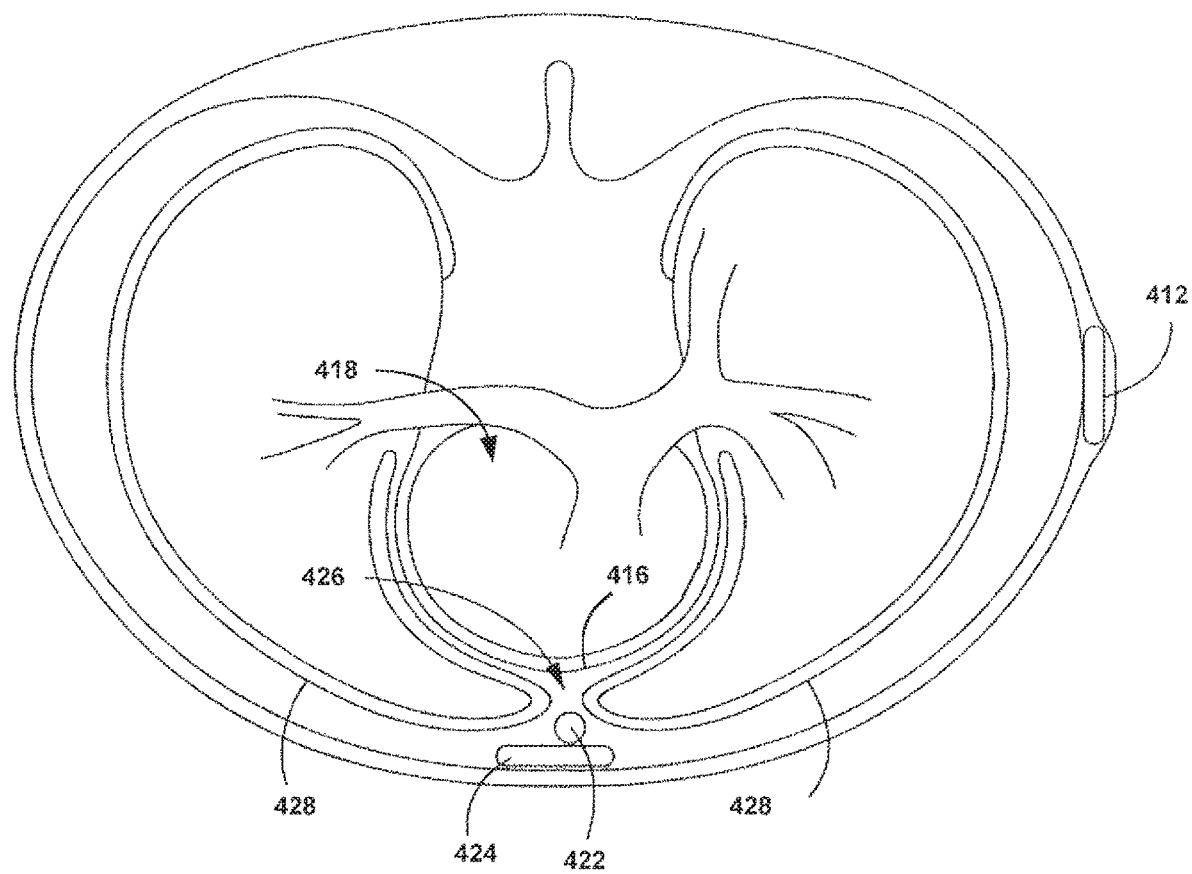
FIG. 18C is a conceptual drawing illustrating a transverse view of the patient with the example medical system of FIG. 18A.

FIGS. 18A-18C are conceptual diagrams of another example medical system 410 implanted within a patient 408. FIG. 18A is a front view of medical system 410 implanted within patient 408. FIG. 18B is a side view of medical system 410 implanted within patient 408. FIG. 18C is a transverse view of medical device system 410 implanted within patient 408.

In some examples, the medical system 410 is an extravascular implantable cardioverter-defibrillator (EV-ICD) system implanted within patient 408. Medical system 410 includes IMD 412, which in the illustrated example is implanted subcutaneously or submuscularly on the left midaxillary of patient 408, such that IMD 412 may be positioned on the left side of patient 408 above the ribcage. In some other examples, IMD 412 may be implanted at other subcutaneous locations on patient 408 such as at a pectoral location or abdominal location. IMD 412 includes housing 420 that may form a hermetic seal that protects components of IMD 412. In some examples, housing 420 of IMD 412 may be formed of a conductive material, such as titanium, or of a combination of conductive and non-conductive materials, which may function as a housing electrode. IMD 412 may also include a connector assembly (also referred to as a connector block or header) that includes electrical feedthroughs through which electrical connections are made between lead 422 and electronic components included within the housing.

IMD 412 may provide the cardiac EGM sensing, asystole detection, and other functionality described herein with respect to IMD 10, and housing 420 may house circuitries 50-62 and an antenna 26 (FIGS. 2 and 3) that provide such functionality. Housing 420 may also house therapy delivery circuitry configured to generate therapeutic electric signals, such as cardiac pacing and anti-tachyarrhythmia shocks, for delivery to patient 408. System 410 may include an external device 12 that may function with IMD 412 as described herein with respect to IMD 10 and system 2.

In the illustrated example, IMD 412 is connected to at least one implantable cardiac lead 422. Lead 422 includes an elongated lead body having a proximal end that includes a connector (not shown) configured to be connected to IMD 412 and a distal portion that includes electrodes 432A, 432B, 434A, and 434B. Lead 422 extends subcutaneously above the ribcage from IMD 412 toward a center of the torso of patient 408. At a location near the center of the torso, lead 422 bends or turns and extends intrathoracically superior under/below sternum 424. Lead 422 thus may be implanted at least partially in a substernal space, such as at a target site between the ribcage or sternum 424 and heart 418. In one such configuration, a proximal portion of lead 422 may be configured to extend subcutaneously from IMD 12 toward sternum 24 and a distal portion of lead 22 may be configured to extend superior under or below sternum 424 in the anterior mediastinum 426 (FIG. 1C).

For example, lead 422 may extend intrathoracically superior under/below sternum 424 within anterior mediastinum 426. Anterior mediastinum 426 may be viewed as being bounded posteriorly by pericardium 416, laterally by pleurae 428, and anteriorly by sternum 424. In some examples, the anterior wall of anterior mediastinum 426 may also be formed by the transversus thoracis and one or more costal cartilages. Anterior mediastinum 426 includes a quantity of loose connective tissue (such as areolar tissue), some lymph vessels, lymph glands, substernal musculature (e.g., transverse thoracic muscle), and small vessels or vessel branches. In one example, the distal portion of lead 422 may be implanted substantially within the loose connective tissue and/or substernal musculature of anterior mediastinum 426. In such examples, the distal portion of lead 422 may be physically isolated from pericardium 416 of heart 418. A lead implanted substantially within anterior mediastinum 426 is an example of a substernal lead or, more generally, an extravascular lead.

The distal portion of lead 422 is described herein as being implanted substantially within anterior mediastinum 426. Thus, some of distal portion of lead 422 may extend out of anterior mediastinum 426 (e.g., a proximal end of the distal portion), although much of the distal portion may be positioned within anterior mediastinum 426. In other embodiments, the distal portion of lead 422 may be implanted intrathoracically in other non-vascular, extra-pericardial locations, including the gap, tissue, or other anatomical features around the perimeter of and adjacent to, but not attached to, the pericardium 416 or other portion of heart 418 and not above sternum 424 or the ribcage. Lead 422 may be implanted anywhere within the "substernal space" defined by the undersurface between the sternum and/or ribcage and the body cavity but not including pericardium 416 or other portions of heart 418. The substernal space may alternatively be referred to by the terms "retrosternal space" or "mediastinum" or "infrasternal" as is known to those skilled in the art and includes the anterior mediastinum 426. The substernal space may also include the anatomical region described in Baudoin, Y. P., et al., entitled "The superior epigastric artery does not pass through Larrey's space (trigonum sternocostale)." Surg.Radiol.Anat. 25.3-4 (2003): 259-62 as Larrey's space. In other words, the distal portion of lead 422 may be implanted in the region around the outer surface of heart 418, but not attached to heart 418. For example, the distal portion of lead 422 may be physically isolated from pericardium 416.

Lead 422 may include an insulative lead body having a proximal end that includes connector 430 configured to be connected to IMD 412 and a distal portion that includes one or more electrodes. As shown in FIG. 18A, the one or more electrodes of lead 422 may include electrodes 432A, 432B, 434A, and 434B, although in other examples, lead 422 may include more or fewer electrodes. Lead 422 also includes one or more conductors that form an electrically conductive path within the lead body and interconnect the electrical connector and respective ones of the electrodes.

Electrodes 432A, 432B may be defibrillation electrodes (individually or collectively "defibrillation electrode(s) 432"). Although electrodes 432 may be referred to herein as "defibrillation electrodes 432," electrodes 432 may be configured to deliver other types of anti-tachyarrhythmia shocks, such as cardioversion shocks. Though defibrillation electrodes 432 are depicted in FIGS. 18A-18C as coil electrodes for purposes of clarity, it is to be understood that defibrillation electrodes 432 may be of other configurations in other examples. Defibrillation electrodes 432 may be located on the distal portion of lead 422, where the distal portion of lead 422 is the portion of lead 422 that is configured to be implanted extravascularly below the sternum 424.

Lead 422 may be implanted at a target site below or along sternum 424 such that a therapy vector is substantially across a ventricle of heart 418. In some examples, a therapy vector (e.g., a shock vector for delivery of anti-tachyarrhythmia shock) may be between defibrillation electrodes 432 and a housing electrode formed by or on IMD 412. The therapy vector may, in one example, be viewed as a line that extends from a point on defibrillation electrodes 432 (e.g., a center of one of the defibrillation electrodes 432) to a point on a housing electrode of IMD 412. As such, it may be advantageous to increase an amount of area across which defibrillation electrodes 432 (and therein the distal portion of lead 422) extends across heart 418. Accordingly, lead 422 may be configured to define a curving distal portion as depicted in FIG. 18A. In some examples, the curving distal portion of lead 22 may help improve the efficacy and/or efficiency of pacing, sensing, and/or defibrillation to heart 418 by IMD 412.

Electrodes 434A, 434B may be pace/sense electrodes (individually or collectively, "pace/sense electrode(s) 434") located on the distal portion of lead 422. Electrodes4 34 are referred to herein as pace/sense electrodes as they generally are configured for use in delivery of pacing pulses and/or sensing of cardiac electrical signals. In some instances, electrodes 434 may provide only pacing functionality, only sensing functionality, or both pacing functionality and sensing functionality. In the example illustrated in FIG. 18A and FIG. 18B, pace/sense electrodes 434 are separated from one another by defibrillation electrode 432B. In other examples, however, pace/sense electrodes 434 may be both distal of defibrillation electrode 432B or both proximal of defibrillation electrode 432B. In examples in which lead 422 includes more or fewer electrodes 432, 434, such electrodes may be positioned at other locations on lead 422.

In the example of FIG. 18A, the distal portion of lead 422 is a serpentine shape that includes two "C" shaped curves, which together may resemble the Greek letter epsilon, "ε." Defibrillation electrodes 432 are each carried by one of the two respective C-shaped portions of the lead body distal portion. The two C-shaped curves extend or curve in the same direction away from a central axis of the lead body. In some examples, pace/sense electrodes 434 may be approximately aligned with the central axis of the straight, proximal portion of lead 422. In such examples, mid-points of defibrillation electrodes 432 are laterally offset from pace/sense electrodes 434. Other examples of extra-cardiovascular leads including one or more defibrillation electrodes and one or more pace/sense electrodes 434 carried by curving, serpentine, undulating or zig-zagging distal portion of lead 422 also may be implemented using the techniques described herein. In some examples, the distal portion of lead 422 may be straight (e.g., straight or nearly straight).

Deploying lead 422 such that electrodes 432, 434 are at the depicted peaks and valleys of serpentine shape may provide access to preferred sensing or therapy vectors. Orienting the serpentine shaped lead such that pace/sense electrodes 434 are closer to heart 418 may provide better electrical sensing of the cardiac signal and/or lower pacing capture thresholds than if pace/sense electrodes 434 were oriented further from heart 418. The serpentine or other shape of the distal portion of lead 422 may have increased fixation to patient 408 as a result of the shape providing resistance against adjacent tissue when an axial force is applied. Another advantage of a shaped distal portion is that electrodes 432, 434 may have access to greater surface area over a shorter length of heart 418 relative to a lead having a straighter distal portion.

In some examples, the elongated lead body of lead 422 may include one or more elongated electrical conductors (not illustrated) that extend within the lead body from the connector at the proximal lead end to electrodes 432, 434 located along the distal portion of lead 422. The one or more elongated electrical conductors contained within the lead body of lead 422 may engage with respective ones of electrodes 432, 434. The conductors may electrically couple to circuitry, such as a therapy delivery circuitry and sensing circuitry 52, of IMD 412 via connections in connector assembly. The electrical conductors transmit therapy from the therapy delivery circuitry to one or more of electrodes 432, 434, and transmit sensed cardiac EGMs from one or more of electrodes 432, 434 to sensing circuitry 52 within IMD 412.

In general, IMD 412 may sense cardiac EGMs, such as via one or more sensing vectors that include combinations of pace/sense electrodes 434 and/or a housing electrode of IMD 412. In some examples, IMD 412 may sense cardiac EGMs using a sensing vector that includes one or both of the defibrillation electrodes 432 and/or one of defibrillation electrodes 432 and one of pace/sense electrodes 434 or a housing electrode of IMD 412. Medical system 410, including processing circuitry of IMD 412 and/or external device 12, may perform any of the techniques described herein for determining whether asystole detection and false asystole detection criteria are satisfied, e.g., based on cardiac EGMs sensed via extravascular electrodes 432, 434. Cardiac EGMs sensed via extravascular electrodes may include noise, e.g., due to changing contact with tissue and/or orientation relative to heart, in a similar manner as described herein with respect to subcutaneous electrodes. In general, when electrodes are not fixed directly to the myocardium, motion, e.g., respiratory motion, can cause variability in depolarization amplitudes and other noise that may lead to false asystole detections. The techniques described herein may be implemented with cardiac EGMs sensed via subcutaneous electrodes, cutaneous electrodes, substernal electrodes, extravascular electrodes, intra-muscular electrodes, or any electrodes positioned in (or in contact with) any tissue of a patient.

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, DRAM, SRAM, magnetic discs, optical discs, flash memories, or forms of EPROM or EEPROM. The instructions may be executed to support one or more aspects of the functionality described in this disclosure.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

What is claimed is:

1. A medical system comprising:
a plurality of electrodes configured to sense a cardiac electrogram of a patient; and
processing circuitry configured to:
determine that an asystole detection criterion is satisfied based on not identifying a cardiac depolarization in the cardiac electrogram during a time interval;
based on the determination that the asystole detection is satisfied, determine whether a plurality of false asystole detection criteria are satisfied based on the cardiac electrogram signal; and
withhold an indication of an asystole episode for the patient based on a determination that at least one of the plurality of false asystole detection criteria is satisfied,
wherein the plurality of false asystole detection criteria comprises:
a first false asystole detection criterion including a reduced amplitude threshold for detecting cardiac depolarizations in the cardiac electrogram; and
a second false asystole detection criterion for detecting decaying noise in the cardiac electrogram, and
wherein, to determine that the first false asystole detection criterion is satisfied, the processing circuitry is configured to:
identify a plurality of cardiac depolarizations occurring in the cardiac electrogram preceding the time interval;
determine an amplitude for each cardiac depolarization of the plurality of identified cardiac depolarizations;
determine the reduced amplitude threshold based on the determined amplitudes of the plurality of identified cardiac depolarizations.

2. The medical system of claim 1, wherein, to determine that the first false asystole detection criterion is satisfied, the processing circuitry is configured to:
compare the reduced amplitude threshold to the cardiac electrogram during the time interval; and
determine that a threshold number of cardiac depolarizations is identified in the cardiac electrogram during the time interval based on the comparison.

3. The medical system of claim 1, wherein the processing circuitry is configured to:
determine a representative amplitude based on the amplitudes of each the plurality of identified cardiac depolarizations; and
determine the reduced amplitude threshold as a predetermined portion of the representative amplitude.

4. The medical system of claim 1, wherein, to determine that the second false asystole detection criterion is satisfied, the processing circuitry is configured to:
calculate an area-under-the-curve value for the cardiac electrogram during at least a portion of the time interval; and
determine that the area-under-the-curve value satisfies an area-under-the-curve threshold.

5. The medical system of claim 1, wherein, to determine that the second false asystole detection criterion is satisfied, the processing circuitry is configured to:
determine a differential signal of the cardiac electrogram during at least a portion of the time interval;
for each of a plurality of samples of the differential signal, determine whether a sign of the sample is positive or negative; and
determine that an amount of samples having one of the signs satisfies a common sign threshold.

6. The medical system of claim 1, wherein the plurality of false asystole detection criteria further comprises a third false asystole detection criterion, wherein, to determine that the third false asystole detection criterion is satisfied, the processing circuitry is configured to:
- identify a plurality of cardiac depolarizations occurring in the cardiac electrogram preceding the time interval;
- determine an amplitude for each of the plurality of identified cardiac depolarizations;
- determine a variability of the amplitudes; and
- determine that the variability satisfies a variability threshold.

7. The medical system of claim 6, wherein, to determine the variability of the amplitudes, the processing circuitry is configured to:
- determine a maximum amplitude of the plurality of amplitudes;
- determine a representative amplitude of the plurality of amplitudes; and
- determine a metric of comparison of the maximum amplitude to the representative amplitude.

8. The medical system of claim 1, wherein the plurality of false asystole detection criteria further comprises a third false asystole detection criterion, wherein, to determine that the third false asystole detection criterion is satisfied, the processing circuitry is configured to:
- identify a plurality of cardiac depolarizations occurring in the cardiac electrogram preceding the time interval;
- determine one or more intervals between adjacent ones of the plurality of cardiac depolarizations;
- based on the determined intervals, identify one or more expected cardiac depolarization windows and one or more expected inter-depolarization windows within the time interval;
- determine a first energy of the one or more cardiac depolarization windows and a second energy of the one or more inter-depolarization windows;
- determine a metric of comparison of the first energy to the second energy; and
- determine that the metric of comparison satisfies a threshold.

9. The medical system of claim 1, wherein the processing circuitry is configured to:
- determine a count of instances of satisfaction of the asystole detection criterion within a time period; and
- determine whether the count satisfies at least one asystole count criterion,
- wherein the processing circuitry is configured to determine whether the plurality of false asystole detection criteria are satisfied based on determining that the count satisfies at least one asystole count criterion.

10. The medical system of claim 1, wherein the plurality of electrodes are configured for subcutaneous implantation, and the cardiac electrogram comprises a subcutaneous cardiac electrogram.

11. The medical system of claim 1, wherein the plurality of electrodes are configured for extravascular implantation, and the cardiac electrogram comprises an extravascular cardiac electrogram.

12. A method comprising:
- sensing a cardiac electrogram of a patient via a plurality of electrodes of a medical system;
- determining, by processing circuitry of the medical system, that an asystole detection criterion is satisfied based on not identifying a cardiac depolarization in the cardiac electrogram during a time interval;
- based on the determination that the asystole detection is satisfied, determining, by the processing circuitry, that at least one of a plurality of false asystole detection criteria are satisfied based on the cardiac electrogram signal; and
- withholding, by the processing circuitry, an indication of an asystole episode for the patient based on a determination that at least one of the plurality of false asystole detection criteria is satisfied,
- wherein the plurality of false asystole detection criteria comprises:
  - a first false asystole detection criterion including a reduced amplitude threshold for detecting cardiac depolarizations in the cardiac electrogram;
  - a second false asystole detection criterion for detecting decaying noise in the cardiac electrogram, and
  - wherein determining that the first false asystole detection criterion is satisfied comprises:
    - identifying, by the processing circuitry, one or more cardiac depolarizations occurring in the cardiac electrogram preceding the time interval;
    - determining, by the processing circuitry, an amplitude for each of the one or more identified cardiac depolarizations; and
    - determining by the processing circuitry, the reduced amplitude threshold based on the determined amplitudes of the one or more identified cardiac depolarizations.

13. The method of claim 12, wherein determining that the first false asystole detection criterion is satisfied comprises:
- comparing the reduced amplitude threshold to the cardiac electrogram during the time interval; and
- determining that a threshold number of cardiac depolarizations is identified in the cardiac electrogram during the time interval based on the comparison.

14. The method of claim 12, wherein determining the reduced amplitude threshold comprises:
- determining a representative amplitude based on the amplitudes of each the plurality of identified cardiac depolarizations; and
- determining the reduced amplitude threshold as a predetermined portion of the representative amplitude.

15. The method of claim 12, wherein determining that the second false asystole detection criterion is satisfied comprises:
- calculating an area-under-the-curve value for the cardiac electrogram during at least a portion of the time interval; and
- determining that the area-under-the-curve value satisfies an area-under-the-curve threshold.

16. The method of claim 12, wherein determining that the second false asystole detection criterion is satisfied comprises:
- determining a differential signal of the cardiac electrogram during at least a portion of the time interval;
- for each of a plurality of samples of the differential signal, determining whether a sign of the sample is positive or negative; and
- determining that an amount of samples having one of the signs satisfies a common sign threshold.

17. The method of claim 12, wherein the plurality of false asystole detection criteria further comprises a third false asystole detection criterion, wherein determining that the third false asystole detection criterion is satisfied comprises:
- identifying a plurality of cardiac depolarizations occurring in the cardiac electrogram preceding the time interval;
- determining an amplitude for each of the plurality of identified cardiac depolarizations;

determining a variability of the amplitudes; and
determining that the variability satisfies a variability threshold.

18. The method of claim 17, wherein determining the variability of the amplitudes comprises:
   determining a maximum amplitude of the plurality of amplitudes;
   determining a representative amplitude of the plurality of amplitudes; and
   determining a metric of comparison of the maximum amplitude to the representative amplitude.

19. The method of claim 12, wherein the plurality of false asystole detection criteria further comprises a third false asystole detection criterion, and determining that the third false asystole detection criterion is satisfied comprises:
   identifying a plurality of cardiac depolarizations occurring in the cardiac electrogram preceding the time interval;
   determining one or more intervals between adjacent ones of the plurality of cardiac depolarizations;
   based on the determined intervals, identifying one or more expected cardiac depolarization windows and one or more expected inter-depolarization windows within the time interval;
   determining a first energy of the one or more cardiac depolarization windows and a second energy of the one or more inter-depolarization windows;
   determining a metric of comparison of the first energy to the second energy; and
   determining that the metric of comparison satisfies a threshold.

20. The method of claim 12, further comprising, by the processing circuitry:
   determining a count of instances of satisfaction of the asystole detection criterion within a time period; and
   determining whether the count satisfies at least one asystole count criterion,
   wherein determining whether the plurality of false asystole detection criteria are satisfied comprises determining whether the plurality of false asystole detection criteria are satisfied based on determining that the count satisfies the at least one asystole count criterion.

21. The method of claim 12, wherein the plurality of electrodes are subcutaneously-implanted, and sensing the cardiac electrogram comprises sensing the cardiac electrogram via the plurality of subcutaneously-implanted electrodes.

22. The method of claim 12, wherein the plurality of electrodes are extravascularly implanted, and sensing the cardiac electrogram comprises sensing the cardiac electrogram via the plurality of extravascularly-implanted electrodes.

23. A non-transitory computer-readable storage medium comprising program instructions that, when executed by processing circuitry of a medical system, cause the processing circuitry to:
   determine that an asystole detection criterion is satisfied based on not identifying a cardiac depolarization in a cardiac electrogram during a time interval sensed via a plurality of electrodes of the medical system;
   based on the determination that the asystole detection is satisfied, determine whether a plurality of false asystole detection criteria are satisfied based on the cardiac electrogram signal; and
   withhold an indication of an asystole episode for the patient based on a determination that at least one of the plurality of false asystole detection criteria is satisfied,
   wherein the plurality of false asystole detection criteria comprises:
      a first false asystole detection criterion including a reduced amplitude threshold for detecting cardiac depolarizations in the cardiac electrogram; and
      a second false asystole detection criterion for detecting decaying noise in the cardiac electrogram, and
      wherein, to determine that the first false asystole detection criterion is satisfied, the processing circuitry is caused to:
         identify a plurality of cardiac depolarizations occurring in the cardiac electrogram preceding the time interval;
         determine an amplitude for each cardiac depolarization of the plurality of identified cardiac depolarizations; and
         determine the reduced amplitude threshold based on the determined amplitudes of the plurality of identified cardiac depolarizations.

* * * * *